(12) United States Patent
Anderson et al.

(10) Patent No.: US 7,858,183 B2
(45) Date of Patent: Dec. 28, 2010

(54) PARTICLES

(75) Inventors: Steven M. Anderson, Worcester, MA (US); Janel Lanphere, Pawtucket, RI (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 980 days.

(21) Appl. No.: 11/070,967

(22) Filed: Mar. 2, 2005

(65) Prior Publication Data

US 2006/0199009 A1    Sep. 7, 2006

(51) Int. Cl.
*A61K 9/50*    (2006.01)
(52) U.S. Cl. .................... 428/402.2; 424/489
(58) Field of Classification Search ............... 428/325, 428/402–402.24; 503/215; 514/2; 264/4–4.7; 424/489; 427/213.3–213.36
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,671,994 A * | 6/1987 | Cochran, Jr. ................ 428/325 |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |

(Continued)

FOREIGN PATENT DOCUMENTS

AU    A-76186/98    10/1998

(Continued)

OTHER PUBLICATIONS

Huang et al., "Hydrophilic-hydrophobic biodegradable polymers: release characteristics of hydrogen-bonded, ring-containing polymer matrices," *Biomaterials*, 15(15):1243-1247 (1994).

(Continued)

*Primary Examiner*—James Seidleck
*Assistant Examiner*—Saira Haider
(74) *Attorney, Agent, or Firm*—Fish & Richardson P.C.

(57) ABSTRACT

A particle with a diameter of at most about 3,000 microns has an internal pressure of at least about 1.1 atmospheres at a temperature of less than about 25° C.

6 Claims, 17 Drawing Sheets

U.S. PATENT DOCUMENTS

| | | |
|---|---|---|
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Solodovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,236,410 A | 8/1993 | Granov et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,710 A | 11/1994 | Asai |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,441,746 A | 8/1995 | Chagnon |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |

| | | | | | | |
|---|---|---|---|---|---|---|
| 5,840,387 | A | 11/1998 | Berlowitz-Tarrant et al. | 6,306,427 | B1 | 10/2001 | Annonier et al. |
| 5,846,518 | A | 12/1998 | Yan et al. | 6,312,407 | B1 | 11/2001 | Zadno-Azizi et al. |
| 5,853,752 | A | 12/1998 | Unger et al. | 6,312,942 | B1 | 11/2001 | Plüss-Wenzinger et al. |
| 5,855,615 | A | 1/1999 | Bley et al. | 6,315,709 | B1 | 11/2001 | Garibaldi et al. |
| 5,863,957 | A | 1/1999 | Li et al. | 6,335,384 | B1 | 1/2002 | Evans et al. |
| 5,876,372 | A | 3/1999 | Grabenkort et al. | 6,344,182 | B1 | 2/2002 | Sutton et al. |
| 5,877,224 | A | 3/1999 | Brocchini et al. | 6,355,275 | B1 | 3/2002 | Klein |
| 5,885,216 | A | 3/1999 | Evans, III et al. | 6,368,658 | B1 | 4/2002 | Schwarz et al. |
| 5,885,547 | A | 3/1999 | Gray | 6,379,373 | B1 | 4/2002 | Sawhney et al. |
| 5,888,546 | A | 3/1999 | Ji et al. | 6,388,043 | B1 | 5/2002 | Langer et al. |
| 5,888,930 | A | 3/1999 | Smith et al. | 6,394,965 | B1 | 5/2002 | Klein |
| 5,891,155 | A | 4/1999 | Irie | 6,410,508 | B1 * | 6/2002 | Isales et al. ................... 514/2 |
| 5,894,022 | A | 4/1999 | Ji et al. | 6,423,332 | B1 | 7/2002 | Huxel et al. |
| 5,895,398 | A | 4/1999 | Wensel et al. | 6,432,437 | B1 | 8/2002 | Hubbard |
| 5,895,411 | A | 4/1999 | Irie | 6,436,112 | B2 | 8/2002 | Wensel et al. |
| 5,899,877 | A | 5/1999 | Leibitzki et al. | 6,443,941 | B1 | 9/2002 | Slepian et al. |
| 5,902,832 | A | 5/1999 | Van Bladel et al. | 6,458,296 | B1 | 10/2002 | Heinzen et al. |
| 5,902,834 | A | 5/1999 | Porrvik | 6,476,069 | B2 | 11/2002 | Krall et al. |
| 5,922,025 | A | 7/1999 | Hubbard | 6,495,155 | B1 | 12/2002 | Tice et al. |
| 5,922,304 | A | 7/1999 | Unger | 6,544,503 | B1 | 4/2003 | Vanderhoff et al. |
| 5,928,626 | A | 7/1999 | Klaveness et al. | 6,544,544 | B2 | 4/2003 | Hunter et al. |
| 5,935,553 | A | 8/1999 | Unger et al. | 6,545,097 | B2 | 4/2003 | Pinchuk et al. |
| 5,951,160 | A | 9/1999 | Ronk | 6,565,887 | B1 | 5/2003 | Gray et al. |
| 5,957,848 | A | 9/1999 | Sutton et al. | 6,575,896 | B2 | 6/2003 | Silverman et al. |
| 5,959,073 | A | 9/1999 | Schlameus et al. | 6,586,364 | B2 * | 7/2003 | Kubota et al. ............... 503/215 |
| 6,003,566 | A | 12/1999 | Thibault et al. | 6,602,261 | B2 | 8/2003 | Greene, Jr. et al. |
| 6,015,546 | A | 1/2000 | Sutton et al. | 6,602,524 | B2 | 8/2003 | Batich et al. |
| 6,027,472 | A | 2/2000 | Kriesel et al. | 6,605,111 | B2 | 8/2003 | Bose et al. |
| 6,028,066 | A | 2/2000 | Unger | 6,629,947 | B1 | 10/2003 | Sahatjian et al. |
| 6,047,861 | A | 4/2000 | Vidal et al. | 6,632,531 | B2 | 10/2003 | Blankenship |
| 6,048,908 | A | 4/2000 | Kitagawa | 6,652,883 | B2 | 11/2003 | Goupil et al. |
| 6,051,247 | A | 4/2000 | Hench et al. | 6,680,046 | B1 | 1/2004 | Boschetti |
| 6,056,721 | A | 5/2000 | Shulze | 6,699,222 | B1 | 3/2004 | Jones et al. |
| 6,056,844 | A | 5/2000 | Guiles et al. | 6,706,394 | B2 | 3/2004 | Kuehnle et al. |
| 6,059,766 | A | 5/2000 | Greff | 2001/0001835 | A1 | 5/2001 | Greene, Jr. et al. |
| 6,063,068 | A | 5/2000 | Fowles et al. | 2001/0016210 | A1 | 8/2001 | Mathiowitz et al. |
| 6,071,495 | A | 6/2000 | Unger et al. | 2001/0036451 | A1 | 11/2001 | Goupil et al. |
| 6,071,497 | A | 6/2000 | Steiner et al. | 2001/0051670 | A1 | 12/2001 | Goupil et al. |
| 6,073,759 | A | 6/2000 | Lamborne et al. | 2002/0054912 | A1 | 5/2002 | Kim et al. |
| 6,090,925 | A | 7/2000 | Woiszwillo et al. | 2002/0061954 | A1 | 5/2002 | Davis et al. |
| 6,096,344 | A | 8/2000 | Liu et al. | 2002/0160109 | A1 | 10/2002 | Yeo et al. |
| 6,099,864 | A | 8/2000 | Morrison et al. | 2002/0182190 | A1 | 12/2002 | Naimark et al. |
| 6,100,306 | A | 8/2000 | Li et al. | 2002/0197208 | A1 | 12/2002 | Ruys et al. |
| 6,139,963 | A | 10/2000 | Fujii et al. | 2003/0007928 | A1 | 1/2003 | Gray |
| 6,149,623 | A | 11/2000 | Reynolds | 2003/0032935 | A1 | 2/2003 | Damiano et al. |
| 6,160,084 | A | 12/2000 | Langer et al. | 2003/0108614 | A1 | 6/2003 | Volkonsky et al. |
| 6,162,377 | A | 12/2000 | Ghosh et al. | 2003/0163187 | A1 | 8/2003 | Weber |
| 6,165,193 | A | 12/2000 | Greene, Jr. et al. | 2003/0183962 | A1 | 10/2003 | Buiser et al. |
| 6,167,313 | A | 12/2000 | Gray et al. | 2003/0185895 | A1 | 10/2003 | Lanphere et al. |
| 6,179,817 | B1 | 1/2001 | Zhong | 2003/0185896 | A1 | 10/2003 | Buiser et al. |
| 6,191,193 | B1 | 2/2001 | Lee et al. | 2003/0187320 | A1 | 10/2003 | Freyman |
| 6,214,331 | B1 | 4/2001 | Vanderhoff et al. | 2003/0194390 | A1 | 10/2003 | Krall et al. |
| 6,214,384 | B1 | 4/2001 | Pallado et al. | 2003/0203985 | A1 | 10/2003 | Baldwin et al. |
| 6,224,630 | B1 | 5/2001 | Bao et al. | 2003/0206864 | A1 | 11/2003 | Mangin |
| 6,224,794 | B1 | 5/2001 | Amsden et al. | 2003/0215519 | A1 | 11/2003 | Schwarz et al. |
| 6,235,224 | B1 | 5/2001 | Mathiowitz et al. | 2003/0233150 | A1 | 12/2003 | Bourne et al. |
| 6,238,403 | B1 | 5/2001 | Greene, Jr. et al. | 2004/0076582 | A1 | 4/2004 | Dimatteo et al. |
| 6,245,090 | B1 | 6/2001 | Gilson et al. | 2004/0091543 | A1 | 5/2004 | Bell et al. |
| 6,251,661 | B1 | 6/2001 | Urabe et al. | 2004/0092883 | A1 | 5/2004 | Casey, III et al. |
| 6,258,338 | B1 | 7/2001 | Gray | 2004/0096662 | A1 | 5/2004 | Lanphere et al. |
| 6,261,585 | B1 | 7/2001 | Sefton et al. | 2004/0101564 | A1 | 5/2004 | Rioux et al. |
| 6,264,861 | B1 | 7/2001 | Tavernier et al. | 2004/0186377 | A1 | 9/2004 | Zhong et al. |
| 6,267,154 | B1 | 7/2001 | Felicelli et al. | 2005/0025800 | A1 | 2/2005 | Tan |
| 6,268,053 | B1 | 7/2001 | Woiszwillo et al. | 2005/0037047 | A1 | 2/2005 | Song |
| 6,277,392 | B1 | 8/2001 | Klein | 2005/0095428 | A1 | 5/2005 | Dicarlo et al. |
| 6,280,457 | B1 | 8/2001 | Wallace et al. | 2005/0129775 | A1 | 6/2005 | Lanphere et al. |
| 6,291,605 | B1 | 9/2001 | Freeman et al. | 2005/0196449 | A1 | 9/2005 | Dicarlo et al. |
| 6,296,604 | B1 | 10/2001 | Garibaldi et al. | 2005/0226935 | A1 | 10/2005 | Kamath et al. |
| 6,296,622 | B1 | 10/2001 | Kurz et al. | 2005/0238870 | A1 | 10/2005 | Buiser et al. |
| 6,296,632 | B1 | 10/2001 | Luscher et al. | | | | |
| 6,306,418 | B1 | 10/2001 | Bley | | | | |
| 6,306,419 | B1 | 10/2001 | Vachon et al. | | | | |
| 6,306,425 | B1 | 10/2001 | Tice et al. | | | | |

2005/0263916 A1 12/2005 Lanphere et al.

FOREIGN PATENT DOCUMENTS

| | | |
|---|---|---|
| DE | 3834705 | 4/1990 |
| DE | 42 01 461 | 7/1993 |
| DE | 94 14 868 | 12/1994 |
| DE | 297 24 255 U1 | 10/2000 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 993 337 | 4/2000 |
| ES | 2 096 521 | 3/1997 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/28090 | 9/1996 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/21772 | 5/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/66183 | 11/2000 |
| WO | WO 00/71196 | 11/2000 |
| WO | WO 00/74633 | 12/2000 |
| WO | WO 01/12359 | 2/2001 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | WO 01/93920 | 12/2001 |
| WO | WO 02/11696 | 2/2002 |
| WO | WO 02/34298 | 5/2002 |
| WO | WO 02/34299 | 5/2002 |
| WO | WO 02/34300 | 5/2002 |
| WO | WO 02/43580 | 6/2002 |
| WO | WO 03/013552 | 2/2003 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/020042 | 3/2004 |
| WO | WO 2004/040972 | 5/2004 |
| WO | WO 2004/073688 | 9/2004 |
| WO | WO 2004/075989 | 9/2004 |

OTHER PUBLICATIONS

U.S. Appl. No. 10/927,868, filed Aug. 27, 2004, Richard et al.
U.S. Appl. No. 11/000,741, filed Dec. 1, 2004, Elliott et al.
U.S. Appl. No. 11/274,538, filed Nov. 15, 2005, Tenney et al.
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.
Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.
Barr, J.D., et al., "Polyvinyl Alcohol Foam Particles Sizes and Concentrations Injectable through Microcatheters", *JVIR*, vol. 9, No. 1, pp. 113-118; 1998.
Barton, P. et al., "Embolization of Bone Metastases," *Journal of Vascular and Interventional Radiology*, 7(1):81-88 (Jan.-Feb. 1996).
Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.
Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.
Berenstein, A. et al., "Catheter and Material Selection for Transarterial Embolization: Technical Considerations. II. Materials.", *Radiology*, vol. 132, No. 3, pp. 631-639; 1979.
Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.
Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.
Bourke et al., "Protein Drug Release from Photocrosslinked Poly(vinyl alcohol) Hydrogels," *Society for Biomaterials 28th Annual Meeting Transactions*, p. 144 (2002).
Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11 c antibody with [88]Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/reference.html.

Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996.

Burczak, et al., "Polymeric materials for biomedical purposes obtained by radiation methods. V. hybrid artificial pancreas", *Polim Med*, vol. 24, No. 1-2, pp. 45-55, 1994 (English Summary included).

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Choe, et al., "An experimental study of embolic effect according to infusion rate and concentration of suspension in transarterial particulate embolization", *Invest Radiol*, vol. 32, No. 5, pp. 260-270, 1997.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", *Clinical Therapeutics*, vol. 14, Suppl. A, 1992.

Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.

Colombo M, "Treatment of Hepatocellular Carcinoma", *Journal of Viral Hepatitis*, 4(Suppl. 1):125-130 (1997), http://home.texoma.net/~moreland/stats/hcc-9.html.

Concentric Medical, Inc.—Product Information (3 pages), 2002.

Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Derdeyn, et al., "Collagen-coated acrylic microspheres for embolotherapy: in vivo and in vitro characteristics", *American Journal of Neuroradiology*, vol. 18, No. 4, pp. 647-653, 1997.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

"Fibroid Treatment Collective—Fibroid Embolization," 2 pages, http://www.fibroids.org.

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J Neuroradiol.*, 17:1901-1906 (Nov. 1996).

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Horak et al., "Hydrogels in endovascular embolization. I. Spherical particles of poly (2-hydroxyethyl methacrylate) and their medico-biological properties", *Biomaterials*, 7(3):188-192 (May 1986).

Horak et al., "Hydrogels in endovascular embolization. II. Clinical use of spherical particles",*Biomaterials*, 7(6):467-470 (Nov. 1986).

Huang, et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (English Abstract included).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim, et al., "Composite poly(vinyl alcohol) beads for controlled drug delivery", *Pharm Res*, vol. 9. No. 1, pp. 10-16, 1992.

Kim et al., "Hollow Silica Spheres of Controlled Size and Porosity by Sol-Gel Processing," *J. Am. Ceram. Soc.*, 74(8):1987-1992 (Aug. 1991).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alchohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol *Core Enhances Cellular Proliferation and Vascular Wall Thickness: An In Vitro and In Vivo Study",* Neurosurgery, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Partices", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LFet al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orienti et al., "Crosslinked Polyvinylalcohol Hydrogels as Vehicles for Hydrophilic Drugs," Arch. Pharm. Pharm. Med. Chem., 333:421-424 (2000).

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pedley et al., "Hydrogels in Biomedical Applications," *British Polymer Journal*, 12:99-110 (Sep. 1980).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", *J Neurosurg*, vol. 77, No. 2, pp. 217-222, 1992.

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CDO-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tian et al., "Design and synthesis of amphiphilic poly (ethylene glycol) derivatives as micellar drug delivery systems," *Polymer Preprints*, 43(2):719-720 (Fall 2002).

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variocele and its treatment," http://www.hsc.sunysb.edu/urology/male_inf... variocoele_and_its_treatment.html, 8 pages, Last Updated on Mar. 12, 2001.

Vivas S et al., "Arterioportal fistula and hemobilia in a patient with hepatic transplant" Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grantid=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

U.S. Appl. No. 10/927,868, filed Aug. 27, 2004.
U.S. Appl. No. 11/000,741, filed Dec. 1, 2004.
U.S. Appl. No. 11/111,511, filed Apr. 21, 2005.
U.S. Appl. No. 11/117,156, filed Apr. 28, 2005.
U.S. Appl. No. 11/154,106, filed Jun. 15, 2005.
U.S. Appl. No. 11/165,949, filed Jun. 24, 2005.
U.S. Appl. No. 11/248,033, filed Oct. 12, 2005.
U.S. Appl. No. 11/248,493, filed Oct. 12, 2005.
U.S. Appl. No. 11/311,617, filed Dec. 19, 2005.
U.S. Appl. No. 11/314,056, filed Dec. 21, 2005.
U.S. Appl. No. 11/314,557, filed Dec. 21, 2005.

"Fibroid Treatment Collective—Fibroid Embolization," 2 pages, http://www.fibroids.org.

Kochan, J.P. et al. "Interventional Neuroradiology: Current Practices and Techniques at Temple University Hostipal," http://www.temple.edu/radiology/stroke.html, 5 pages.

Physician' Desk Reference Family Guide to Women's Health, "Chapter 7—Common Disorders of the Reproductive System," http://www.healthsquare.com/pdrfg/wh/chapters/wh1ch01.htm, 24 pages.

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm. 2 pages.

SIR-Spheres (Yttrium-90 Microsphers), pp. 1-12.

UCLA Radiological Sciences, "A summary of terms appearing in this text," http://www.radsci.ucla.edu:8000/aneurysm/terms.html, 1 page.

Vogel F, "Nonsurgical Management of Uterine Fibroids," http://www.holyname.org/brochure/fibroids.html, 5 pages.

Akunets et al., "Super-High-Strength Microballoons for Hydrogen Strorage," International Journal of Hydrogen Energy, Elsevier Science Publishers, vol. 19, No. 8, pp. 697-700, (1994).

Jordan et al., "Magnetic Fluid Hyperthermia (MFH)," Scientific and Clinical Applications of Magnetic Carriers, pp. 569-595, (1997).

Unger et al., "Therapeutic applications of lipid-coated microbubbles," Advanced Drug Delivery Reviews May 7, 2004 Netherlands, vol. 56, No. 9, pp. 1291-1314, May 7, 2004.

International Search Report and Written Opinion, issued in the PCT application: PCT/US2006/007100, filed Feb. 28, 2006.

International Preliminary Report on Patentability, issued in the PCT application: PCT/US2006/007100, filed Feb. 28, 2006.

\* cited by examiner

PARTICLES

TECHNICAL FIELD

The invention relates to particles, as well as related compositions and methods.

BACKGROUND

Energy, such as RF energy, can be employed (e.g., in a tissue ablation procedure) to degrade unhealthy or unwanted tissue, such as warts, moles, cysts, scar tissue, and/or tumors. In some cases, for example, an RF electrode can be delivered into the unhealthy or unwanted tissue via a catheter. Once positioned within the tumor, RF-emitting tines can be deployed and activated. Upon activation, the tines can emit RF energy to degrade the tissue by, for example, heating the tissue.

SUMMARY

In one aspect, the invention features a particle with a diameter of at most about 3,000 microns and an internal pressure of at least about 1.1 atmospheres at a temperature of less than about 25° C. (e.g., at a temperature of about 20° C.).

In another aspect, the invention features a particle including a gas generator and having a diameter of at most about 3,000 microns. When the gas generator is heated to a temperature of at least about 35° C., the internal pressure of the particle increases to at least about 1.5 atmospheres.

In an additional aspect, the invention features a composition including a carrier fluid and particles disposed within the carrier fluid. The particles have an arithmetic mean diameter of at most about 3,000 microns. The environment surrounding the composition has a pressure of at least about 1.1 atmospheres (e.g., from about 1.1 atmospheres to about 1.5 atmospheres).

In a further aspect, the invention features a composition including a carrier fluid and particles disposed within the carrier fluid. The particles have an arithmetic mean diameter of at most about 3,000 microns. The temperature of the environment surrounding the composition is at most about 20° C. (e.g., at most about 10° C.).

In another aspect, the invention features a capsule including at least one particle having a diameter of at most about 3,000 microns and an internal pressure of at least about 1.1 atmospheres at a temperature of less than about 25° C. (e.g., at a temperature of about 20° C.). The capsule has a maximum dimension of from about 3,000 microns to about 5,000 microns.

In an additional aspect, the invention features a method that includes exposing a particle with an internal pressure of at least about 1.1 atmospheres at a temperature of less than about 25° C. (e.g., at a temperature of about 20° C.) to a temperature of at least about 35° C. The particle has a diameter of at most about 3,000 microns.

In a further aspect, the invention features a method including increasing the internal pressure of a particle by at least about five percent (e.g., from about five percent to about 50 percent). The particle has a diameter of at most about 3,000 microns.

In another aspect, the invention features a method that includes exposing a particle to a first temperature of at most about 20° C. (e.g., from about 0° C. to about 20° C., from about 4° C. to about 20° C.), and exposing the particle to a second temperature of at least about 35° C. (e.g., at least about 37° C., at least about 90° C.) to burst the particle. The particle has a diameter of at most about 3,000 microns.

In an additional aspect, the invention features a method that includes delivering a particle with a diameter of at most about 3,000 microns, and an internal pressure of about 1.5 atmospheres at a temperature of about 35° C., into the tissue of a subject.

In a further aspect, the invention features a method of making a particle that has an internal pressure of at least about 1.1 atmospheres at a temperature of less than about 25° C. (e.g., at a temperature of about 20° C.), and a diameter of at most about 3,000 microns. The method includes forming a particle precursor in an environment having a pressure of at least about 1.1 atmospheres, and coating the particle precursor to form the particle.

In another aspect, the invention features a method of making a particle having an internal pressure of at least about 1.1 atmospheres at a temperature of less than about 25° C. and a diameter of at most about 3,000 microns. The method includes forming the particle at a temperature of at most about 20° C.

Embodiments may also include one or more of the following.

In certain embodiments, the particle can include (e.g., encapsulate) one or more gases, such as carbon dioxide, nitrogen, oxygen, or water vapor.

In certain embodiments, the particle can have an internal pressure of at least about 1.1 atmospheres at a temperature of about 20° C., at least about 1.2 atmospheres at a temperature of about 25° C., at least about 1.3 atmospheres at a temperature of about 30° C., and/or at least about 1.5 atmospheres at a temperature of at least about 35° C. In some embodiments, the particle can have an internal pressure of at least about 1.5 atmospheres at a temperature of at least about 90° C. (e.g., from about 90° C. to about 95° C.).

When the particle is heated to a temperature of at least about 25° C. (e.g., at least about 35° C., at least about 90° C.), the internal pressure of the particle can increase by at least about five percent (e.g., at least about 10 percent, at least about 20 percent, at least about 30 percent, at least about 40 percent).

In some embodiments, the particle can burst at a temperature of at least about 35° C. (e.g., at least about 90° C., from about 90° C. to about 95° C.), and/or at an internal pressure of at least about 1.2 atmospheres (e.g., at least about 1.3 atmospheres, at least about 1.4 atmospheres, at least about 1.5 atmospheres). The particle can include a gas generator, and when the gas generator is heated to a temperature of at least about 25° C. (e.g., at least about 30° C., at least about 35° C., at least about 90° C., at least about 100° C.), the internal pressure of the particle can increase. For example, when the gas generator is heated to a temperature of from about 90° C. to about 95° C., the internal pressure of the particle can increase. In certain embodiments, the internal pressure of the particle can increase to at least about 1.2 atmospheres (e.g., at least about 1.3 atmospheres, at least about 1.4 atmospheres, at least about 1.5 atmospheres), and/or by at least about five percent (e.g., at least about 10 percent, at least about 20 percent, at least about 30 percent, at least about 40 percent). In some embodiments, the internal pressure of the particle can increase by from about five percent to about 50 percent.

The gas generator can include, for example, dry ice, ice, water, and/or saline. The gas generator can be disposed in an interior region of the particle, and/or can be disposed within one or more pores of the particle. When exposed to a temperature of at least about 25° C. (e.g., at least about 30° C., at least about 35° C.), the gas generator can generate gas (e.g., carbon dioxide, water vapor).

The particle can include one or more thermally conductive materials, such as a metal (e.g., iron, aluminum, cobalt, copper, silver, molybdenum, zinc, gold, iridium) or a metal alloy (e.g., steel). In some embodiments, the particle can include a non-metal thermally conductive material, such as silicon or carbon. In certain embodiments, the particle can include one or more electrically conductive materials, such as a metal (e.g., silver, copper, gold, aluminum, iridium, zinc, iron, nickel, molybdenum, cobalt) or a metal alloy (e.g., steel). In certain embodiments, the particle can include one or more materials that are both thermally conductive and electrically conductive, such as silver, copper, gold, aluminum, iridium, molybdenum, zinc, or steel.

In some embodiments, the particle can include a polymer, such as a polyvinyl alcohol, a polyacrylic acid, a polymethacrylic acid, a poly vinyl sulfonate, a carboxymethyl cellulose, a hydroxyethyl celluloses, a substituted cellulose, a polyacrylamide, a polyethylene glycol, a polyamide, a polyurea, a polyurethane, a polyester, a polyether, a polystyrene, a polysaccharide, a polylactic acid, a polyethylene, a polymethylmethacrylate, a polycaprolactone, a polyglycolic acid, a poly(lactic-co-glycolic) acid (e.g., a poly(d-lactic-co-glycolic) acid), or a copolymer or mixture thereof.

In some embodiments, the particle can include a gelling precursor, such as alginate, an alginate salt, a xanthan gum, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, or amylopectin. For example, the particle can include sodium alginate.

The particle can include a ferromagnetic material. In some embodiments, at least some of the ferromagnetic material can be disposed within an interior region of the particle. The ferromagnetic material can be a transition metal (e.g., nickel, cobalt, iron), a metal alloy (e.g., Mu-metal), or a metal oxide (e.g., magnetite). In certain embodiments, the ferromagnetic material can be a soft ferrite, a rare-earth magnet alloy, or an amorphous and non-earth alloy. The ferromagnetic material can be, for example, in the shape of at least one article that is a particle, fiber, flake, or powder, and/or that has a diameter of from about two microns to about 20 microns.

In some embodiments in which the particle includes a ferromagnetic material, exposing the particle to a temperature of at least about 35° C. can cause at least some of the ferromagnetic material to be released from the particle. At least some of the ferromagnetic material can be released into the tissue of a subject.

The particle can be porous. The particle can have a porous region. The pore density of an interior region of the particle can be greater than the pore density of an exterior region of the particle.

The particle can include a coating. The coating can have a thickness of at most 0.02 inch (e.g., from 0.001 inch to 0.02 inch). In certain embodiments, the coating can have a thickness of at most 0.004 inch (e.g., from 0.00004 inch to 0.004 inch).

The particle can be substantially spherical.

The capsule can include a plurality of particles, and/or can have an internal pressure of at least about 1.1 atmospheres.

Exposing the particle to a temperature of least about 35° C. (e.g., at least about 37° C., at least about 90° C.) can cause the internal pressure of the particle to increase to at least about 1.5 atmospheres, and/or can cause the particle to burst. The particle can be exposed to a temperature of at least about 35° C. (e.g., at least about 37° C., at least about 90° C.) by delivering the particle into the tissue of a subject (e.g., tissue that includes a tumor). Delivering a particle into the tissue of a subject can include exposing the particle to an external pressure of at least about one atmosphere. In some embodiments, exposing the particle to a temperature of at least about 35° C. (e.g., at least about 37° C., at least about 90° C.) can include heating the particle. In certain embodiments, an RF electrode can be used to heat the particle. In some embodiments, the method can further include ablating at least a portion of the tissue of the subject. In certain embodiments, increasing the internal pressure of the particle by at least about five percent can cause the particle to burst.

The method can further include contacting the particle with an agent (e.g., an alcohol, hydrochloric acid, sodium hydroxide, sodium citrate, sodium hexa-metaphosphate) that can dissolve or erode at least a portion of the particle.

The particle can include a therapeutic agent. Exposing the particle to a temperature of at least about 35° C. (e.g., at least about 37° C., at least about 90° C.) can include releasing the therapeutic agent from the particle.

Embodiments can include one or more of the following advantages.

In some embodiments, the particle can enhance tissue heating and/or ablation procedures. For example, in embodiments in which the particle includes a ferromagnetic material, the ferromagnetic material can be released from the particle when the particle bursts at a target site (e.g., within the tissue of a subject). In certain embodiments, the ferromagnetic material can be delivered to the target site relatively quickly, and/or can be distributed relatively uniformly throughout and/or on top of the target site. When exposed to RF radiation, the ferromagnetic material can become heated and, in turn, can heat (e.g., ablate) the target site (e.g., the tissue). A relatively uniform distribution of the ferromagnetic material throughout and/or on top of the target site can provide for relatively even ablation of the target site and, correspondingly, for a relatively uniform and consistent burn.

In certain embodiments, the particle can be used to deliver one or more therapeutic agents (e.g., drugs) to a target site relatively efficiently and effectively. For example, once delivered to a target site, the particle can burst, and can thereby release therapeutic agent. In some embodiments, the particle can be used to deliver a therapeutic agent directly to the target site, such that the therapeutic agent can have an immediate effect on the target site. In certain embodiments, the particle can provide for the relatively wide and/or uniform distribution of therapeutic agent at a target site.

In some embodiments, the particle can be used both to enhance tissue heating and/or ablation procedures, and to provide one or more therapeutic agents to a target site. For example, a particle can include both a ferromagnetic material and a therapeutic agent. When the particle bursts at a target site, the particle can release the ferromagnetic material and the therapeutic agent to the target site, such that the ferromagnetic material can be used in a tissue heating/ablation procedure, and the therapeutic agent can be used to treat the target site.

Features and advantages are in the description, drawings, and claims.

DETAILED DESCRIPTION

Figure 1A:
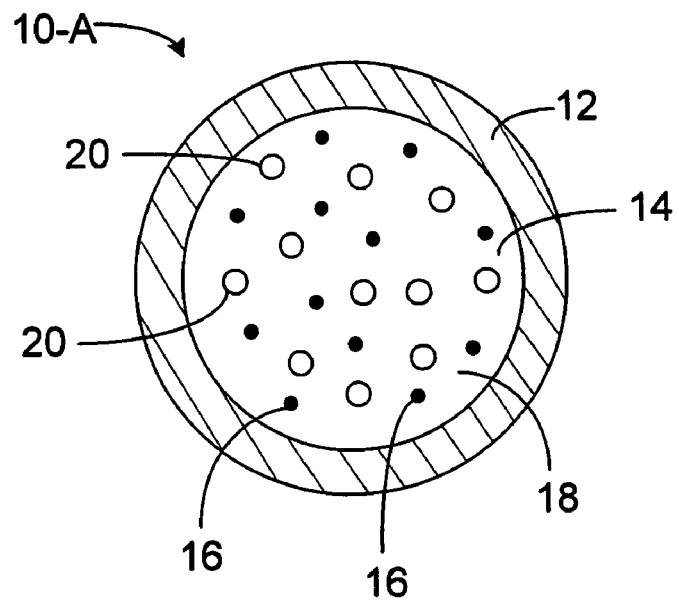
FIG. 1A is a cross-sectional view of an embodiment of a particle.

FIG. 1A shows a particle 10-A at a temperature of less than about 25° C. Particle 10-A has a coating 12 that encloses an interior region 14 formed of a matrix 18 and ferromagnetic particles 16. Pockets 20 of carbon dioxide gas are dispersed throughout matrix 18. At a temperature of less than about 25° C., particle 10-A has an internal pressure of at least about 1.1 atmospheres.

Figure 1B:
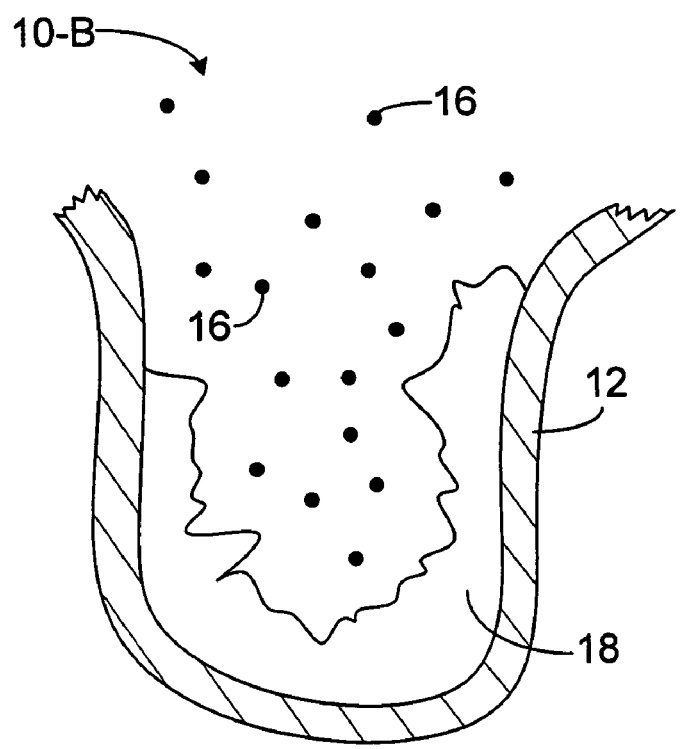
FIG. 1B is a cross-sectional view of the particle of FIG. 1A, as the particle is bursting.

FIG. 1B shows a burst particle 10-B, which is the result of the exposure of particle 10-A to a temperature of at least about 35° C. The increase in temperature results in an increase in the pressure of the carbon dioxide gas within pockets 20, and thus in the internal pressure of particle 10-A. This increase in internal pressure eventually causes particle 10-A to burst, forming burst particle 10-B. When particle 10-A bursts, it releases ferromagnetic particles 16.

In general, the internal pressure of particle 10-A at a given temperature can be selected so that when particle 10-A is heated to a certain higher temperature, particle 10-A will burst. In some embodiments, at a temperature of less than about 25° C., particle 10-A can have an internal pressure of at least about 1.1 atmospheres (e.g., at least about 1.2 atmospheres, at least about 1.3 atmospheres, at least about 1.4 atmospheres, at least about 1.5 atmospheres, at least about two atmospheres, at least about three atmospheres, at least about four atmospheres), and/or at most about five atmospheres (e.g., at most about four atmospheres, at most about three atmospheres, at most about two atmospheres, at most about 1.5 atmospheres, at most about 1.4 atmospheres, at most about 1.3 atmospheres, at most about 1.2 atmospheres). In certain embodiments, at a temperature of less than about 25° C. (e.g., at a temperature of from about 0° C. to about 20° C., at a temperature of from about 4° C. to about 20° C., at a temperature of about 20° C.), particle 10-A can have an internal pressure of from about 1.1 atmospheres to about 1.5 atmospheres.

Generally, as the temperature of the environment surrounding particle 10-A (and, therefore, the temperature of particle 10-A itself) increases, the internal pressure of particle 10-A can also increase. In certain embodiments, the increase in the temperature of particle 10-A (e.g., to at least about 25° C., at least about 35° C., or at least about 90° C.) can cause the internal pressure of particle 10-A to increase by at least about five percent (e.g., at least about 10 percent, at least about 20 percent, at least about 30 percent, at least about 40 percent). For example, the internal pressure of particle 10-A can increase by from about five percent to about 50 percent as the temperature of particle 10-A increases (e.g., to at least about 25° C., at least about 35° C., or at least about 90° C.). In some embodiments, the increase in the temperature of particle 10-A can cause the internal pressure of particle 10-A to increase to at least about 1.2 atmospheres (e.g., at least about 1.3 atmospheres, at least about 1.4 atmospheres, at least about 1.5 atmospheres).

In some embodiments, particle 10-A can burst when the internal pressure of particle 10-A is at least about 1.1 atmospheres (e.g., at least about 1.2 atmospheres, at least about 1.3 atmospheres, at least about 1.4 atmospheres, at least about 1.5 atmospheres, at least about two atmospheres, at least about three atmospheres, at least about four atmospheres), and/or at most about five atmospheres (e.g., at most about four atmospheres, at most about three atmospheres, at most about two atmospheres, at most about 1.5 atmospheres, at most about 1.4 atmospheres, at most about 1.3 atmospheres, at most about 1.2 atmospheres). In certain embodiments, particle 10-A can be designed to burst once particle 10-A has reached a predetermined internal pressure.

In some embodiments, particle 10-A can be designed to burst once particle 10-A has reached a predetermined temperature. In certain embodiments, particle 10-A can burst at a temperature of at least about 20° C. (e.g., at least about 25° C., at least about 30° C., at least about 35° C., at least about 40° C., at least about 50° C., at least about 60° C., at least about 70° C., at least about 80° C., at least about 90° C., at least about 100° C., at least about 125° C., at least about 150° C., at least about 175° C.), and/or at most about 200° C. (e.g., at most about 175° C., at most about 150° C., at most about 125° C., at most about 100° C., at most about 90° C., at most about 80° C., at most about 70° C., at most about 60° C., at most about 50° C., at most about 40° C., at most about 35° C., at most about 30° C., at most about 25° C.). For example, particle 10-A can burst at about 37° C.

The temperature at which particle 10-A bursts can be selected, for example, based on the application(s) for which particle 10-A is being used. For example, if particle 10-A is being used for an RF ablation procedure (such as the procedure described below with reference to FIGS. 2A-2E), it may be desirable for particle 10-A to remain intact until the target site has been sufficiently heated. In some embodiments in which particle 10-A is to be used in an ablation procedure, particle 10-A may be designed to burst at a temperature of at least about 90° C. (e.g., from about 90° C. to about 95° C.).

Typically, the thickness of coating 12 of particle 10-A can be selected to accommodate an increase in the internal pressure of particle 10-A to a predetermined level, at which point particle 10-A may burst. In some embodiments, coating 12 can have a thickness of at most 0.02 inch (e.g., at most 0.01 inch, at most 0.005 inch, at most 0.004 inch), and/or at least 0.00004 inch (e.g., at least 0.004 inch, at least 0.005 inch, at least 0.01 inch). For example, coating 12 may have a thickness of from 0.00004 inch to 0.02 inch (e.g., from 0.001 inch to 0.02 inch).

Coating 12 and matrix 18 of particle 10-A can be formed of the same materials or different materials. In some embodiments, coating 12 and/or matrix 18 can be formed of at least one polymer and/or at least one non-polymer. In certain embodiments, coating 12 and/or matrix 18 can be formed of at least gelling precursor. In general, coating 12 and/or matrix 18 can be formed of one or more materials that are biocompatible, bioerodible, and/or bioabsorbable.

Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides (e.g., nylon), polyureas, polyurethanes, polyesters, polyethers, polystyrenes, polysaccharides (e.g., alginate, agarose), polylactic acids, polyethylenes, polymethylmethacrylates, polyethylacrylate, polycaprolactones, polyglycolic acids, poly(lactic-co-glycolic) acids (e.g., poly(d-lactic-co-glycolic) acids), and copolymers or mixtures thereof. In certain embodiments, the polymer can be a highly water insoluble, high molecular weight polymer. An example of such a polymer is a high molecular weight polyvinyl alcohol (PVA) that has been acetalized. The polymer can be substantially pure intrachain 1,3-acetalized PVA and substantially free of animal derived residue such as collagen.

Examples of gelling precursors include alginates, alginate salts (e.g. sodium alginate), xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. A preferred sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel.

Examples of bioerodible and/or bioabsorbable materials include polysaccharides (e.g., alginate); polysaccharide derivatives; inorganic, ionic salts; water soluble polymers (e.g., polyvinyl alcohol, such as polyvinyl alcohol that has not been cross-linked); biodegradable poly DL-lactide-poly ethylene glycol (PELA); hydrogels (e.g., polyacrylic acid, haluronic acid, gelatin, carboxymethyl cellulose); polyethylene glycol (PEG); chitosan; polyesters (e.g., polycaprolactones); poly(lactic-co-glycolic) acid (e.g., a poly(d-lactic-co-glycolic) acid); and combinations thereof. In some embodiments, a coating can include sodium alginate.

In certain embodiments in which a coating is formed of a bioerodible and/or bioabsorbable material, the coating can begin to erode once it has been delivered into the body. For example, the coating may be designed to erode upon contact with blood. The erosion of the coating can result in a reduction in the thickness of the coating, which can accelerate the bursting of the particle once the internal pressure of the particle has reached a predetermined level. In some embodiments in which a coating is formed of one or more bioerodible and/or bioabsorbable materials, the coating can be relatively thick prior to delivery to a target site. This thickness can, for example, provide enhanced durability to the particle during storage and/or delivery.

In certain embodiments, a particle can include multiple (e.g., two, three, four, five) coatings formed of one or more of the materials described above.

Ferromagnetic particles 16 can include one type ferromagnetic material, or multiple types of ferromagnetic materials. In some embodiments, some ferromagnetic particles 16 are formed of one type of ferromagnetic material, while others ferromagnetic particles 16 are formed of a different type of ferromagnetic material. As used herein, a ferromagnetic material refers to a material that has a magnetic susceptibility of at least about 0.075 or more (e.g., at least about 0.1 or more; at least about 0.2 or more; at least about 0.3 or more; at least about 0.4 or more; at least about 0.5 or more; at least about one or more; at least about 10 or more; at least about 100 or more; at least about 1,000 or more; at least about 10,000 or more) when measured at 25° C. A ferromagnetic material can be, for example, a metal (e.g., a transition metal such as nickel, cobalt, or iron), a metal alloy (e.g., a nickel-iron alloy such as Mu-metal), a metal oxide (e.g., an iron oxide such as magnetite), a ceramic nanomaterial, a soft ferrite (e.g., nickel-zinc-iron), a magnet alloy (e.g., a rare earth magnet alloy such as a neodymium-iron-boron alloy or a samarium-cobalt alloy), an amorphous alloy (e.g., iron-silicon-boron), a non-earth alloy, or a silicon alloy (e.g., an iron-zirconium-copper-boron-silicon alloy, an iron-zirconium-copper-boron-silicon alloy). Magnetite is commercially available from FerroTec Corporation (Nashua, N.H.), under the tradename EMG 1111 Ferrofluid. Iron-copper-niobium-boron-silicon alloys are commercially available from Hitachi Metals of America under the tradename Finemet™. Iron-zirconium-copper-boron-silicon alloys are commercially available from MAGNETEC GmbH under the tradename Nanoperm®. Typically, the ferromagnetic material can be a biocompatible material. In some embodiments, the ferromagnetic material is a bioerodible material, such that the material can eventually break down in the body and either be dispersed throughout the body or excreted from the body. In certain embodiments, the ferromagnetic material may not be biocompatible. In such embodiments, the ferromagnetic material may be encapsulated in a biocompatible material, such as polyvinyl alcohol or sodium alginate.

Typically, the velocity at which ferromagnetic particles 16 exit particle 10-A when particle 10-A bursts can be selected to distribute ferromagnetic particles 16 sufficiently across the target site.

In general, particle 10-A can have a diameter of at most about 3,000 microns (e.g., from about two microns to about 3,000 microns, from about 10 microns to about 3,000 microns, from about 40 microns to about 2,000 microns; from about 100 microns to about 700 microns; from about 500 microns to about 700 microns; from about 100 microns to about 500 microns; from about 100 microns to about 300 microns; from about 300 microns to about 500 microns; from about 500 microns to about 1,200 microns; from about 500 microns to about 700 microns; from about 700 microns to about 900 microns; from about 900 microns to about 1,200 microns). In some embodiments, particle 10-A can have a diameter of at most about 3,000 microns (e.g., at most about 2,500 microns; at most about 2,000 microns; at most about 1,500 microns; at most about 1,200 microns; at most about 1,000 microns; at most about 900 microns; at most about 700 microns; at most about 500 microns; at most about 400 microns; at most about 300 microns; at most about 100 microns), and/or at least about two microns (e.g., at least about 10 microns, at least about 100 microns; at least about 300 microns; at least about 400 microns; at least about 500 microns; at least about 700 microns; at least about 900 microns; at least about 1,000 microns; at least about 1,200 microns; at least about 1,500 microns; at least about 2,000 microns; at least about 2,500 microns).

In certain embodiments, particle 10-A can be substantially spherical. In some embodiments, particle 10-A can have a sphericity of about 0.8 or more (e.g., about 0.85 or more, about 0.9 or more, about 0.95 or more, about 0.97 or more). Particle 10-A can be, for example, manually compressed, essentially flattened, while wet to about 50 percent or less of its original diameter and then, upon exposure to fluid, regain a sphericity of about 0.8 or more (e.g., about 0.85 or more, about 0.9 or more, about 0.95 or more, about 0.97 or more). The sphericity of a particle can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. The sphericity of a particle, which is computed as Da/Dp (where Da=√(4A/π); Dp=P/π; A=pixel area; P=pixel perimeter), is a value from zero to one, with one representing a perfect circle.

Typically, when used, particles 10-A can be disposed within a carrier fluid to form a composition (e.g., a suspension) which can then be delivered to a target site. The carrier fluid can be, for example, a pharmaceutically acceptable carrier, such as saline, contrast agent, therapeutic agent, or a combination of these carriers. In some embodiments, the carrier fluid can include deionized water, water for injection, liquid polymer, gel polymer, gas, or a combination of these carriers.

Compositions that include particles such as particles 10-A can be delivered to various sites in the body, including, for example, sites having cancerous lesions, such as the breast, prostate, lung, thyroid, or ovaries. The compositions can be used in the treatment of, for example, fibroids, tumors, internal bleeding, arteriovenous malformations (AVMs), and/or hypervascular tumors. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted. In some embodiments, a composition containing the particles can be used to prophylactically treat a condition.

The magnitude of a dose of a composition can vary based on the nature, location and severity of the condition to be treated, as well as the route of administration. A physician treating the condition, disease or disorder can determine an effective amount of composition. An effective amount of composition refers to the amount sufficient to result in amelioration of symptoms or a prolongation of survival of the subject. The compositions can be administered as pharmaceutically acceptable compositions to a subject in any therapeutically acceptable dosage, including those administered to a subject intravenously, subcutaneously, percutaneously, intratracheally, intramuscularly, intramucosaly, intracutaneously, intra-articularly, intra-arterially, orally or parenterally.

A composition can include a mixture of particles (e.g., particles that have different internal pressures, particles that include different types of ferromagnetic materials), or can include particles that are all of the same type. In some embodiments, a composition can be prepared with a calibrated concentration of particles for ease of delivery by a physician. A physician can select a composition of a particular concentration based on, for example, the type of procedure to be performed. In certain embodiments, a physician can use a composition with a relatively high concentration of particles during one part of a procedure, and a composition with a relatively low concentration of particles during another part of a procedure.

Suspensions of particles in saline solution can be prepared to remain stable (e.g., to remain suspended in solution and not settle and/or float) over a desired period of time. A suspension of particles can be stable, for example, for from about one minute to about 20 minutes (e.g. from about one minute to about 10 minutes, from about two minutes to about seven minutes, from about three minutes to about six minutes).

In some embodiments, particles can be suspended in a physiological solution by matching the density of the solution to the density of the particles. In certain embodiments, the particles and/or the physiological solution can have a density of from about one gram per cubic centimeter to about 1.5 grams per cubic centimeter (e.g., from about 1.2 grams per cubic centimeter to about 1.4 grams per cubic centimeter, from about 1.2 grams per cubic centimeter to about 1.3 grams per cubic centimeter).

In some embodiments, the carrier fluid of a composition can include a surfactant. The surfactant can help the particles to mix evenly in the carrier fluid and/or can decrease the likelihood of the occlusion of a delivery device (e.g., a catheter) by the particles. In certain embodiments, the surfactant can enhance delivery of the composition (e.g., by enhancing the wetting properties of the particles and facilitating the passage of the particles through a delivery device). In some embodiments, the surfactant can decrease the occurrence of air entrapment by the particles in a composition (e.g., by porous particles in a composition). Examples of liquid surfactants include Tween® 80 (available from Sigma-Aldrich) and Cremophor EL® (available from Sigma-Aldrich). An example of a powder surfactant is Pluronic® F127 NF (available from BASF). In certain embodiments, a composition can include from about 0.05 percent by weight to about one percent by weight (e.g., about 0.1 percent by weight, about 0.5 percent by weight) of a surfactant. A surfactant can be added to the carrier fluid prior to mixing with the particles and/or can be added to the particles prior to mixing with the carrier fluid.

In some embodiments, among the particles delivered to a subject in a composition, the majority (e.g., at least about 50 percent, at least about 60 percent, at least about 70 percent, at least about 80 percent, at least about 90 percent) of the particles can have a diameter of at most about 3,000 microns (e.g., at most about 2,500 microns; at most about 2,000 microns; at most about 1,500 microns; at most about 1,200 microns; at most about 900 microns; at most about 700 microns; at most about 500 microns; at most about 400 microns; at most about 300 microns; at most about 100 microns), and/or at least about 10 microns (e.g., at least about 100 microns; at least about 300 microns; at least about 400 microns; at least about 500 microns; at least about 700 microns; at least about 900 microns; at least about 1,200 microns; at least about 1,500 microns; at least about 2,000 microns; at least about 2,500 microns).

In certain embodiments, the particles delivered to a subject in a composition have an arithmetic mean diameter of at most about 3,000 microns (e.g., at most about 2,500 microns; at most about 2,000 microns; at most about 1,500 microns; at most about 1,200 microns; at most about 900 microns; at most about 700 microns; at most about 500 microns; at most about 400 microns; at most about 300 microns; at most about 100 microns), and/or at least about 10 microns (e.g., at least about 100 microns; at least about 300 microns; at least about 400 microns; at least about 500 microns; at least about 700 microns; at least about 900 microns; at least about 1,200 microns; at least about 1,500 microns; at least about 2,000 microns; at least about 2,500 microns). Exemplary ranges for the arithmetic mean diameter of particles delivered to a subject include from about 100 microns to about 500 microns; from about 100 microns to about 300 microns; from about 300 microns to about 500 microns; from about 500 microns to about 700 microns; and from about 900 microns to about 1,200 microns. In general, the particles delivered to a subject in a composition can have an arithmetic mean diameter in approximately the middle of the range of the diameters of the individual particles, and a variance of at most about 20 percent (e.g., at most about 15 percent, at most about 10 percent).

In some embodiments, the arithmetic mean diameter of the particles delivered to a subject in a composition can vary depending upon the particular condition to be treated. As an example, in embodiments in which the particles in a composition are used to treat a liver tumor, the particles delivered to the subject can have an arithmetic mean diameter of at most about 500 microns (e.g., from about 100 microns to about 300 microns; from about 300 microns to about 500 microns). As another example, in embodiments in which the particles in a composition are used to treat a uterine fibroid, the particles delivered to the subject in a composition can have an arithmetic mean diameter of at most about 1,200 microns (e.g., from about 500 microns to about 700 microns; from about 700 microns to about 900 microns; from about 900 microns to about 1,200 microns).

The arithmetic mean diameter of a group of particles can be determined using a Beckman Coulter RapidVUE Image Analyzer version 2.06 (Beckman Coulter, Miami, Fla.), described above. The arithmetic mean diameter of a group of particles (e.g., in a composition) can be determined by dividing the sum of the diameters of all of the particles in the group by the number of particles in the group.

A particle such as particle 10-A can be used, for example, to enhance tissue heating and/or an ablation procedure. For example, FIGS. 2A-2E illustrate the use of multiple particles 10-A in an ablation procedure that involves the exposure of unhealthy tissue to RF energy to damage or destroy the unhealthy tissue.

Figure 2A:
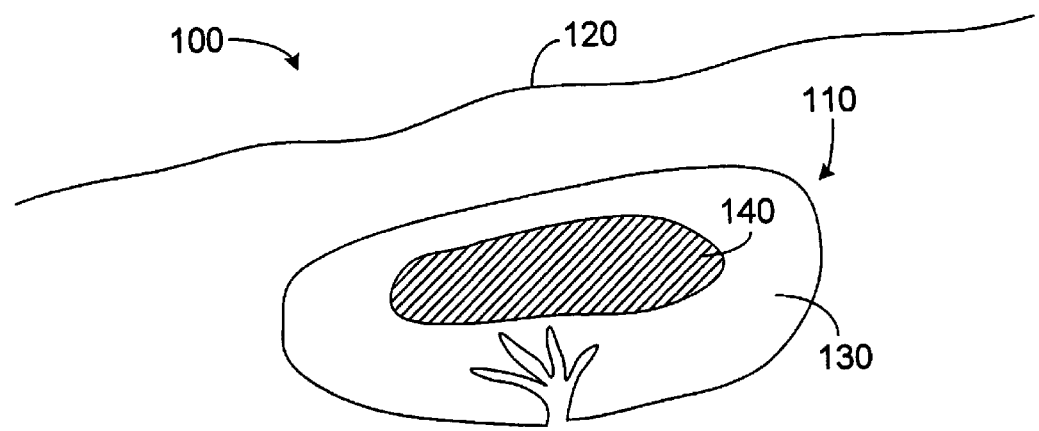
FIG. 2A is a cross-sectional view of a cancerous liver of a subject.
Figure 2B:
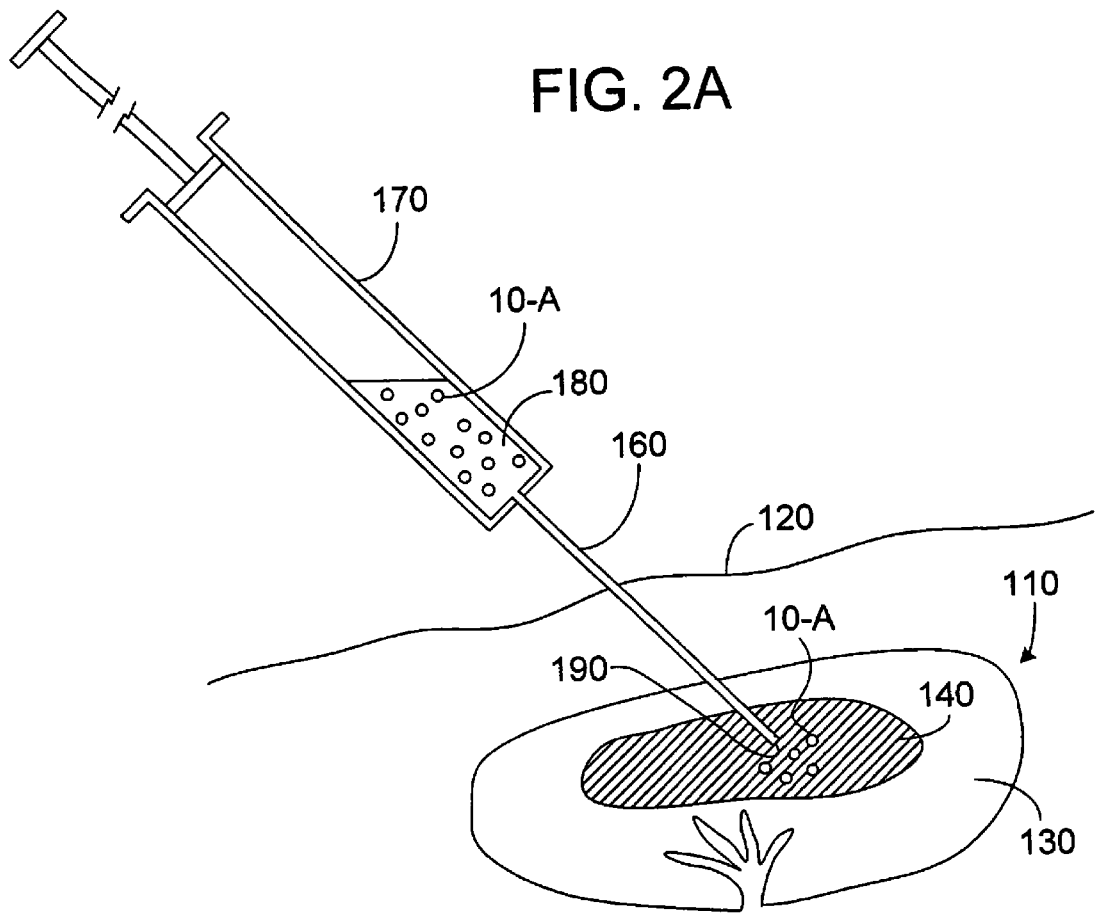
FIG. 2B illustrates administration of the particles of FIG. 1A into the liver of FIG. 2A.

FIG. 2A shows a portion 100 of a subject including a liver 110 and skin 120. Liver 110 includes healthy tissue 130 and unhealthy tissue 140 (e.g., cancerous tissue, such as a cancerous tumor). FIG. 2B illustrates the delivery of particles 10-A into unhealthy tissue 140 of liver 110 using a needle 160. Needle 160 is in fluid communication with a syringe 170, which contains a composition including particles 10-A suspended in a carrier fluid 180. An end 190 of needle 160 is inserted into unhealthy tissue 140, and particles 10-A and carrier fluid 180 are then injected from syringe 170 into unhealthy tissue 140.

In certain embodiments, particles 10-A may not be suspended in a carrier fluid. For example, particles 10-A alone can be contained within syringe 170, and injected from syringe 170 into unhealthy tissue 140.

The pressure and/or temperature within syringe 170 can be selected to limit the extent of premature bursting by particles 10-A (e.g., before particles 10-A have reached unhealthy tissue 140). In some embodiments, the pressure within syringe 170 can be at least about 1.1 atmospheres (e.g., from about 1.1 atmospheres to about 1.5 atmospheres). The pressure within syringe 170 can be selected, for example, to be substantially equal to the internal pressure of particles 10-A. In certain embodiments, the temperature within syringe 170 can be at most about 32° C. (e.g., at most about 20° C.).

While embodiments have been described in which a needle is used to deliver particles 10-A into unhealthy tissue 140, in some embodiments, other delivery devices can be used to deliver particles 10-A into unhealthy tissue 140. As an example, particles 10-A can be delivered into unhealthy tissue 140 directly from a syringe. As another example, particles 10-A can be delivered into unhealthy tissue 140 using a catheter. Alternatively or additionally, particles 10-A can be delivered into unhealthy tissue 140 by using other kinds of techniques. For example, an incision can be made in the subject to gain access to unhealthy tissue 140, and particles 10-A can be deposited directly into unhealthy tissue 140 through the incision.

Figure 2C:
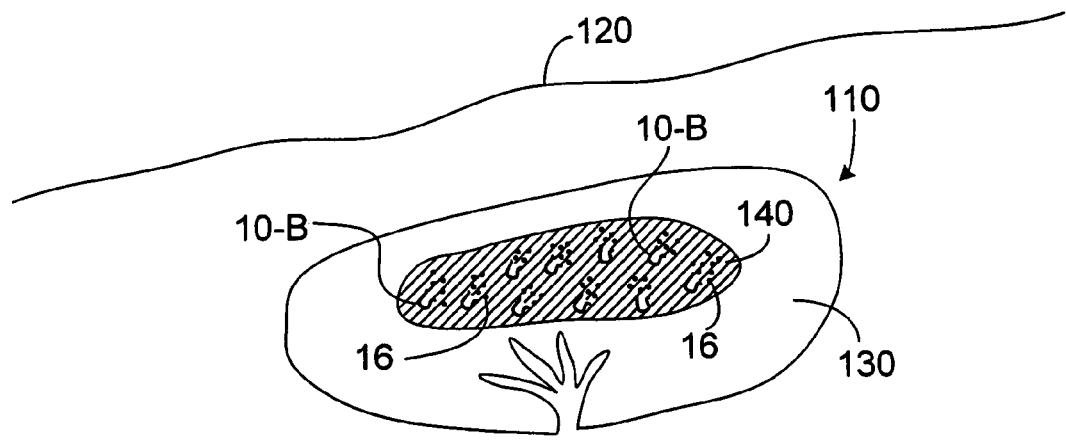
FIG. 2C is a cross-sectional view of the liver of FIGS. 2A and 2B, after the particles have been administered into the liver.
Figure 2D:
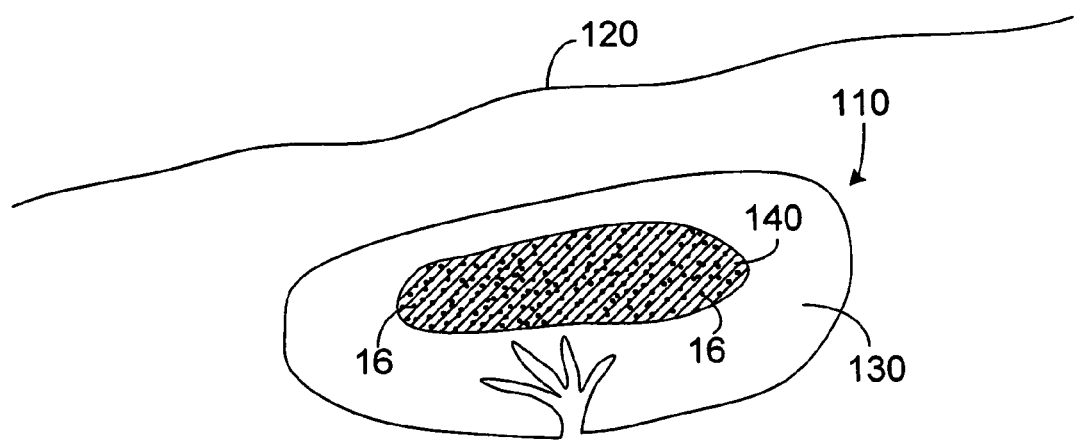
FIG. 2D is a cross-sectional view of the liver of FIGS. 2A, 2B, and 2C, after the particles have burst.

While particles 10-A generally are intact when first delivered into unhealthy tissue 140 (as shown in FIG. 2B), as particles 10-A are heated to body temperature (about 37° C.), particles 10-A burst, forming burst particles 10-B. As shown in FIG. 2C, when particles 10-A burst, they release ferromagnetic particles 16 into unhealthy tissue 140. In certain embodiments in which coating 12 and matrix 18 are formed of a bioerodible or bioabsorbable material (described above), coating 12 and matrix 18 can be eroded and/or absorbed by the body, leaving ferromagnetic particles 16 distributed throughout unhealthy tissue 140 (as shown in FIG. 2D).

Figure 2E:
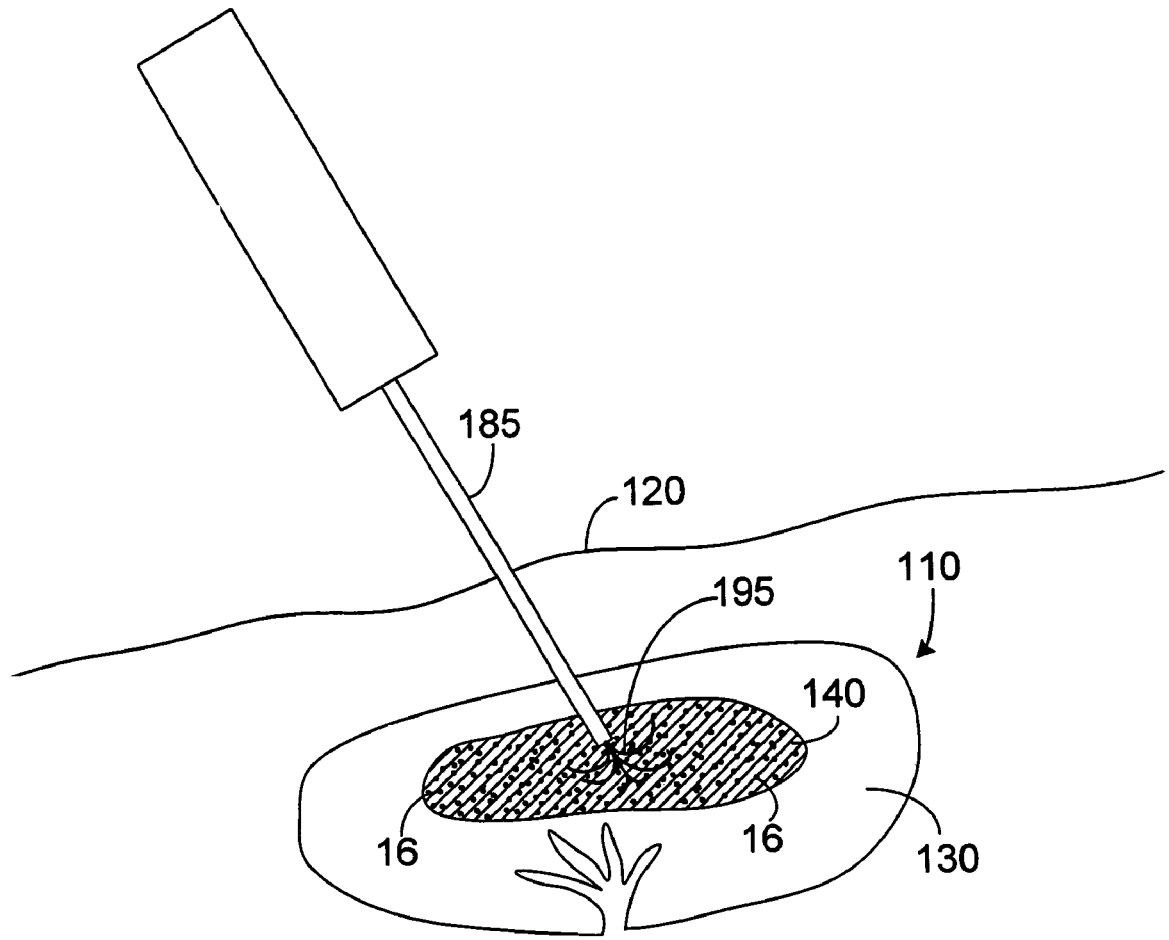
FIG. 2E illustrates an RF electrode with tines deployed within the cancerous tissue region of the liver of FIGS. 2A, 2B, 2C, and 2D.

FIG. 2E illustrates a method of treating unhealthy tissue 140 with RF energy using an RF electrode 185. As shown, RF electrode 185 is positioned within unhealthy tissue 140 (e.g., by insertion through skin 120 of the subject). Once RF electrode 185 is positioned within unhealthy tissue 140, tines 195 of RF electrode 185 are deployed within unhealthy tissue 140, and RF electrode 185 is activated so that RF energy is emitted from tines 195. The RF energy emitted from tines 195 can heat unhealthy tissue 140 around tines 195 to treat (e.g., ablate, damage, destroy) portions of unhealthy tissue 140 that are exposed to the energy.

Various algorithms can be used when exposing the particles to RF energy. In some embodiments, the RF power source is initially set at a power level of 30 Watts, and the power is increased by 10 Watts every minute. In certain embodiments, the RF power source is initially set at a power level of 60 Watts, and the power is increased by 10 Watts every 30 seconds. The end of the procedure can be determined, for example, by the temperature of the ablated tissue and/or by the measured impedance of the RF power circuit. Without wishing to be bound by theory, it is believed that the presence of ferromagnetic particles 16 in unhealthy tissue 140 may enhance the burning of unhealthy tissue 140 (which results in damage or destruction of the tissue) by RF electrode 185.

While certain embodiments of particles have been described, other embodiments of particles can be used to deliver material (e.g., ferromagnetic material, therapeutic agents) to a target site.

Figure 3:
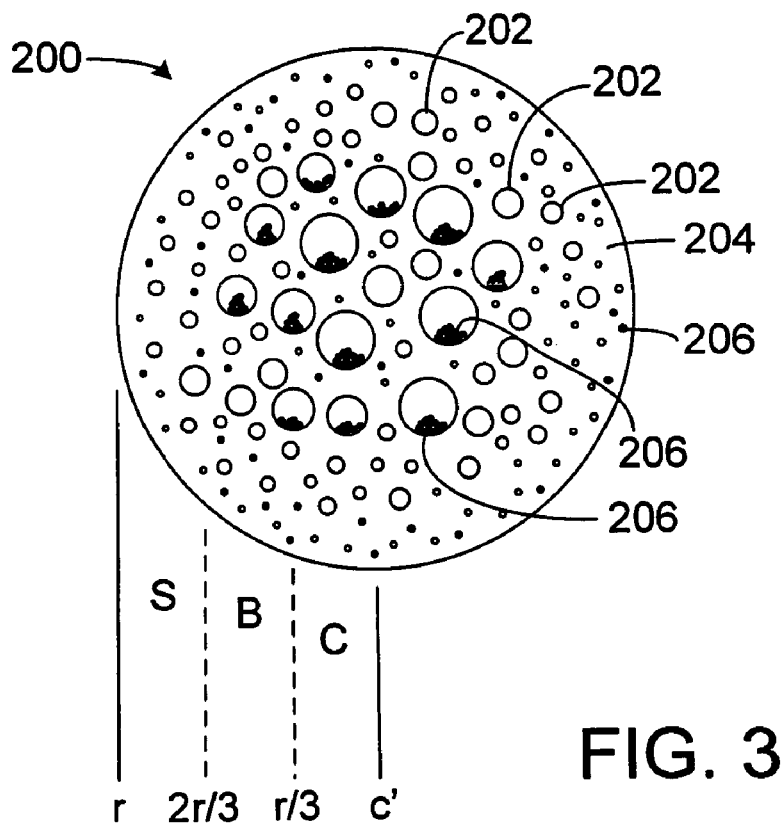
FIG. 3 is a cross-sectional view of an embodiment of a particle.

As an example, FIG. 3 shows a particle 200 that includes pores 202 and a matrix (e.g., a polymer matrix) 204. Ferromagnetic particles 206 are disposed within matrix 204 and some of pores 202. Pores 202 also include one or more gases. Like particle 10-A (FIG. 1A), particle 200 has an internal pressure of at least about 1.1 atmospheres at a temperature of less than about 25° C. When particle 200 is heated to a sufficient temperature, particle 200 bursts, releasing ferromagnetic particles 206.

As shown in FIG. 3, particle 200 can be considered to include a center region, C, from the center c' of particle 200 to a radius of about r/3, a body region, B, from about r/3 to about 2 r/3, and a surface region, S, from about 2 r/3 to r. The regions can be characterized by the relative size of pores 202 present in particle 200 in each region, the density of pores 202 (the number of pores 202 per unit volume of particle 200) in each region, and/or the mass density (the density of matrix 204 and ferromagnetic particles 206 per unit volume of particle 200) in each region.

In general, the mean size of pores 202 in region C of particle 200 is greater than the mean size of pores 202 at region S of particle 200. In some embodiments, the mean size of pores 202 in region C of particle 200 is greater than the mean size of pores 202 in region B particle 200, and/or the mean size of pores 202 in region B of particle 200 is greater than the mean size of pores 202 at region S particle 200. The size of pores 202 in particle 200 can be measured by viewing a cross-section of particle 200. For irregularly shaped (non-spherical) pores, the maximum visible cross-section is used.

Generally, the density of pores 202 in region C of particle 200 is greater than the density of pores 202 at region S of particle 200. In some embodiments, the density of pores 202 in region C of particle 200 is greater than the density of pores 202 in region B of particle 200, and/or the density of pores 202 in region B of particle 200 is greater than the density of pores 202 at region S of particle 200.

In general, the mass density in region C of particle 200 is less than the mass density at region S of particle 200. In some embodiments, the mass density in region C of particle 200 is less than the mass density in region B of particle 200, and/or the mass density in region B of particle 200 is less than the mass density at region S of particle 200. Porous particles are described, for example, in U.S. Patent Application Publication No. US 2003/0185896 A1, published on Oct. 2, 2003, and in U.S. Patent Application Publication No. US 2004/0096662 A1, published on May 20, 2004, both of which are incorporated herein by reference.

Figure 4A:
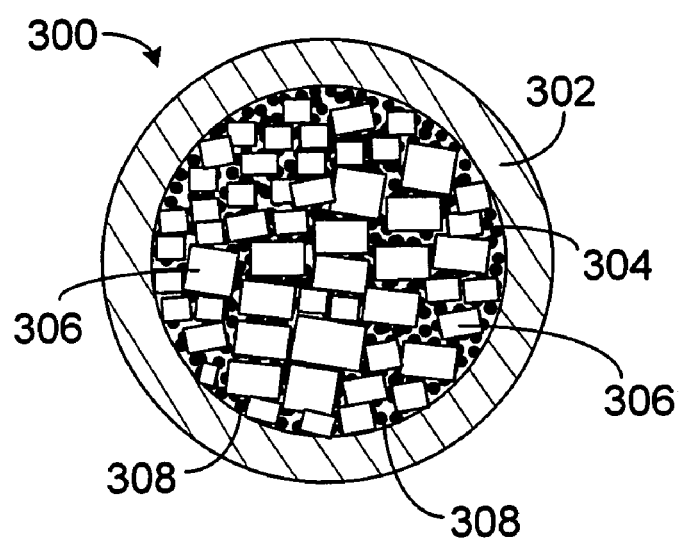
FIG. 4A is a cross-sectional view of an embodiment of a particle.

As another example, in certain embodiments, a particle can include a material that generates a gas, thereby causing the internal pressure of the particle to increase, during the use of the particle. Such a material is referred to herein as a gas generator. In some embodiments, the gas generator can generate gas when the particle (and, therefore, the gas generator) is heated. For example, FIG. 4A shows a particle 300 that has a coating (e.g., a polymer coating) 302 and an interior region 304 including ice pieces 306 and ferromagnetic particles 308. As particle 300 is heated (e.g., when particle 300 is delivered to a target site within a subject), ice pieces 306 melt, producing water. Eventually, if particle 300 is heated to at least about 100° C., the water can produce water vapor, which can cause the internal pressure of particle 300 to increase, until particle 300 bursts, thereby releasing ferromagnetic particles 308.

Figure 4B:
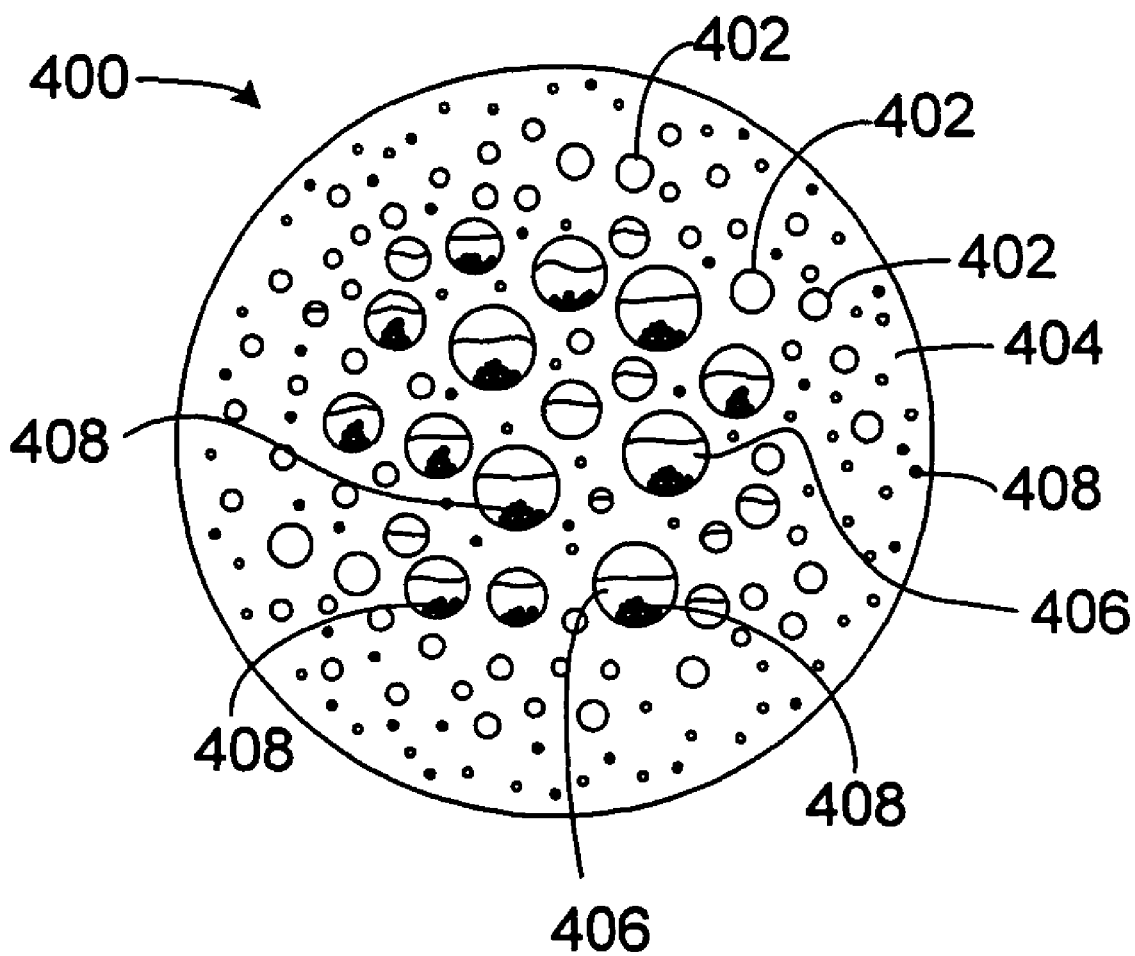
FIG. 4B is a cross-sectional view of an embodiment of a particle.

While ice has been described, in some embodiments, a particle can alternatively or additionally include one or more other types of gas generators that can cause the internal pressure of the particle to increase with an increase in temperature. As an example, a particle can include dry ice or saline. In certain embodiments, a particle can be formed to include water. For example, FIG. 4B shows a particle 400 that includes pores 402 and a matrix (e.g., a polymer matrix) 404. Ferromagnetic particles 408 are dispersed in pores 402 and in matrix 404. Some of pores 402 also contain water. When particle 400 is exposed to a temperature of at least about 100° C., water 406 can produce water vapor that causes the internal pressure of particle 400 to increase. Eventually, particle 400 can burst, thereby releasing ferromagnetic particles 408.

While particles that include ferromagnetic materials have been described, in some embodiments, a particle can alternatively or additionally include one or more other types of materials.

In certain embodiments, a particle can include one or more thermally and/or electrically conductive materials. In such embodiments, the particle may be used to enhance an ablation procedure. Examples of thermally conductive materials include metals (e.g., iron, aluminum, cobalt, copper, silver, molybdenum, zinc, gold, iridium) and metal alloys (e.g., steel). In some embodiments, a particle can include a non-metal thermally conductive material, such as silicon or carbon. Examples of electrically conductive materials include metals (e.g., silver, copper, gold, aluminum, iridium, zinc, iron, nickel, molybdenum, cobalt) and metal alloys (e.g., steel). Examples of materials that are both thermally conductive and electrically conductive include silver, copper, gold, aluminum, iridium, molybdenum, zinc, and steel.

In some embodiments, a particle can include one or more therapeutic agents (e.g., drugs). The therapeutic agent can, for example, be encapsulated within the particle so that when the particle bursts, it releases the therapeutic agent (e.g., to a target site). Alternatively or additionally, in an embodiment of a particle including a coating, the coating can include one or more therapeutic agents. In some embodiments, a particle can have a coating that includes a high concentration of one or more therapeutic agents. One or more of the therapeutic agents can also be loaded into the interior region of the particle. Thus, the surface of the particle can release an initial dosage of therapeutic agent after which the body of the particle can provide a burst release of therapeutic agent. The therapeutic agent on the surface of the particle can be the same as or different from the therapeutic agent in the body of the particle. The therapeutic agent on the surface can be applied by exposing the particle to a high concentration solution of the therapeutic agent. The therapeutic agent coated particle can include another coating over the surface the therapeutic agent (e.g., a degradable and/or bioabsorbable polymer which erodes when the particle is administered). The coating can assist in controlling the rate at which therapeutic agent is released from the particle. For example, the coating can be in the form of a porous membrane. The coating can delay an initial burst of therapeutic agent release. The coating can be applied by dipping or spraying the particle. The coating can include therapeutic agent or can be substantially free of therapeutic agent. The therapeutic agent in the coating can be the same as or different from an agent on a surface layer of the particle and/or within the particle. A polymer coating (e.g. an erodible coating) can be applied to the particle surface in embodiments in which a high concentration of therapeutic agent has not been applied to the particle surface. Coatings are described, for example, in U.S. Patent Application Publication No. US 2004/0076582 A1, published on Apr. 22, 2004, which is incorporated herein by reference.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death.

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, sulfasalazine and mesalamine; antineoplastic/anti-proliferative/anti-mitotic agents such as paclitaxel, 5-fluorouracil, cisplatin, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, anti-thrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them.

Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

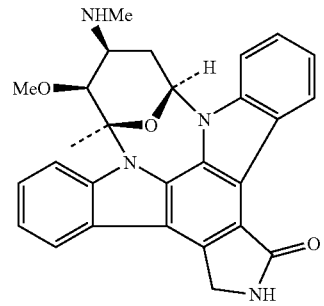

as well as diindoloalkaloids having one of the following general structures:

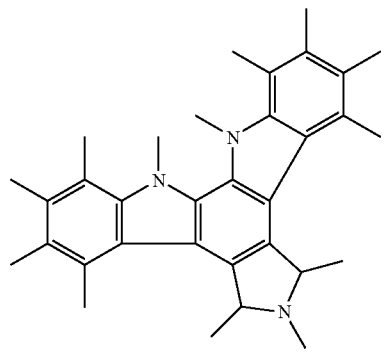

-continued

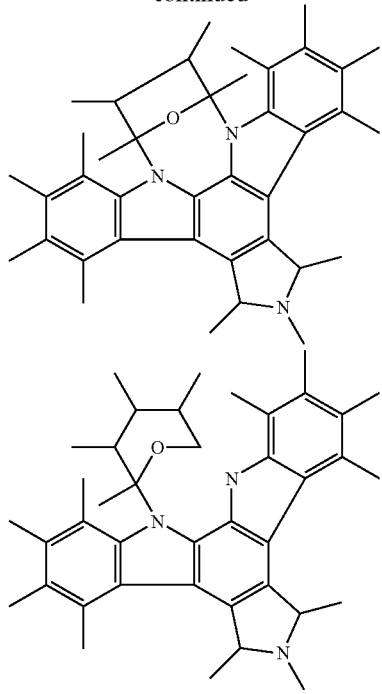

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent").

Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIa inhibitors (e.g., abciximab, epitifibatide, tirofiban); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, transretinoic acid, SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Therapeutic agents are described, for example, in co-pending U.S. Patent Application Publication No. US 2004/0076582 A1, published on Apr. 22, 2004, which is incorporated herein by reference, and in Pinchuk et al., U.S. Pat. No. 6,545,097, incorporated above.

In certain embodiments, in addition to or as an alternative to including one or more therapeutic agents and/or ferromagnetic materials, a particle can include one or more radiopaque materials, materials that are visible by magnetic resonance imaging (MRI-visible materials), and/or ultrasound contrast agents, which are described, for example, in U.S. Patent Application Publication No. US 2004/0101564 A1, published on May 27, 2004, which is incorporated herein by reference.

Particles can be formed by any of a number of different methods.

Figure 5A:
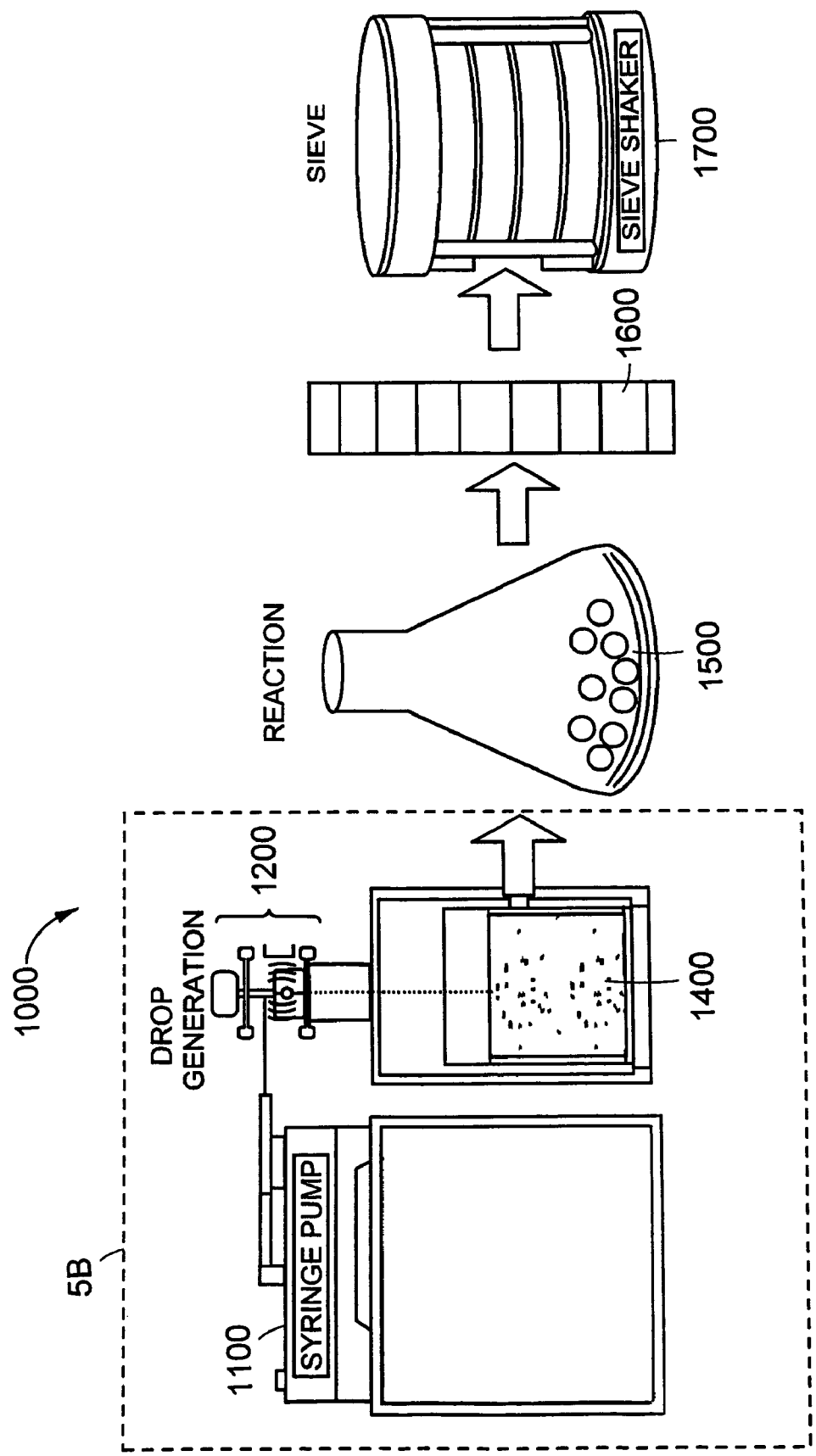
FIG. 5A is a schematic of the manufacture of particles.
Figure 5B:
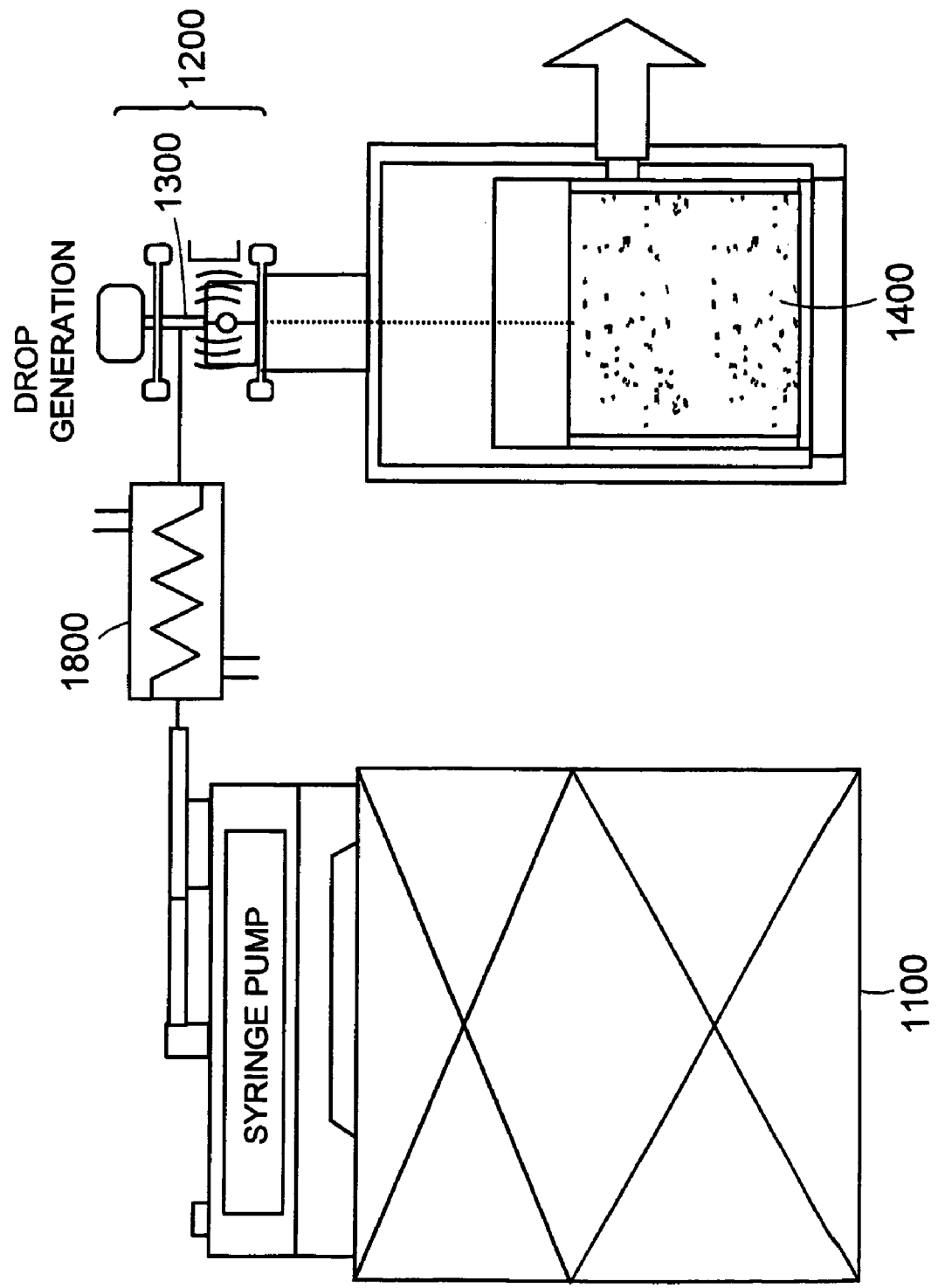
FIG. 5B is an enlarged schematic of region 5B in FIG. 5A.
Figure 6A:
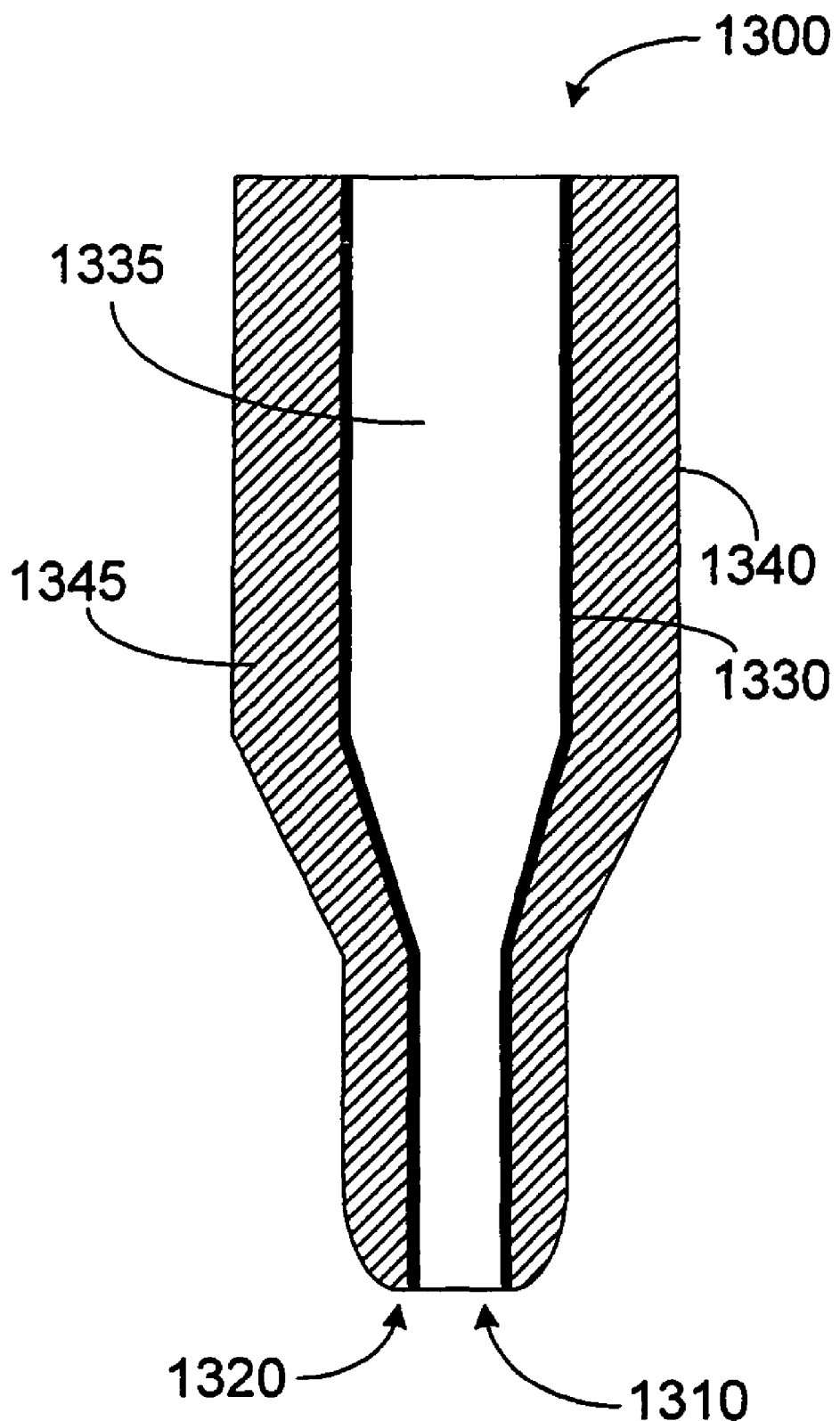
FIG. 6A is a cross-sectional view of an embodiment of an apparatus for producing particles.

As an example, a particle such as particle 10-A (FIG. 1A) can be made using the system 1000 shown in FIGS. 5A and 5B. System 1000 includes a flow controller 1100, a drop generator 1200, a gelling vessel 1400, a reactor vessel 1500, an optional gel dissolution chamber 1600, and a filter 1700. Drop generator 1200 includes a concentric nozzle 1300. As shown in FIG. 6A, concentric nozzle 1300 includes an inner nozzle 1330 with an inner volume 1335 and an orifice 1310. Concentric nozzle 1300 also includes an outer nozzle 1340 with an inner volume 1345 (shaded in FIG. 6A) and an orifice 1320.

Drop generator 1200 can be, for example, the Inotech Encapsulator unit IE-50RINS (Inotech AG, Dottikon, Switzerland), or the model NISCO Encapsulation unit VAR D (NISCO Engineering, Zurich, Switzerland). In some embodiments, concentric nozzle 1300 can be provided as an attachment to drop generator 1200. An example of a concentric nozzle attachment is the model IE-5250 attachment (available from Inotech AG).

Flow controller 1100 delivers a solution (e.g., a polymer solution) and a mixture including ferromagnetic particles 16 (e.g., a gelling precursor mixture) to a viscosity controller 1800, which heats one or both of the solution and the mixture to achieve their respective desired viscosities prior to delivery to drop generator 1200. In certain embodiments, before being transferred to drop generator 1200, one or both of the solution and the mixture can be introduced to a high pressure pumping apparatus, such as a syringe pump (e.g., model PHD4400, Harvard Apparatus, Holliston, Mass.). Alternatively or additionally, drop generator 1200 can contain a pressure control device that applies a pressure (e.g., from about 0.5 Bar to about 1.6 Bar) to one or both of the solution and the mixture (a pressure head) to control the rates at which the solution and/or mixture are transferred to drop generator 1200. Generally, the pressure applied to a given solution or mixture depends on the viscosity of the solution or mixture and/or the desired flow rate of the solution or mixture.

Figure 6B:
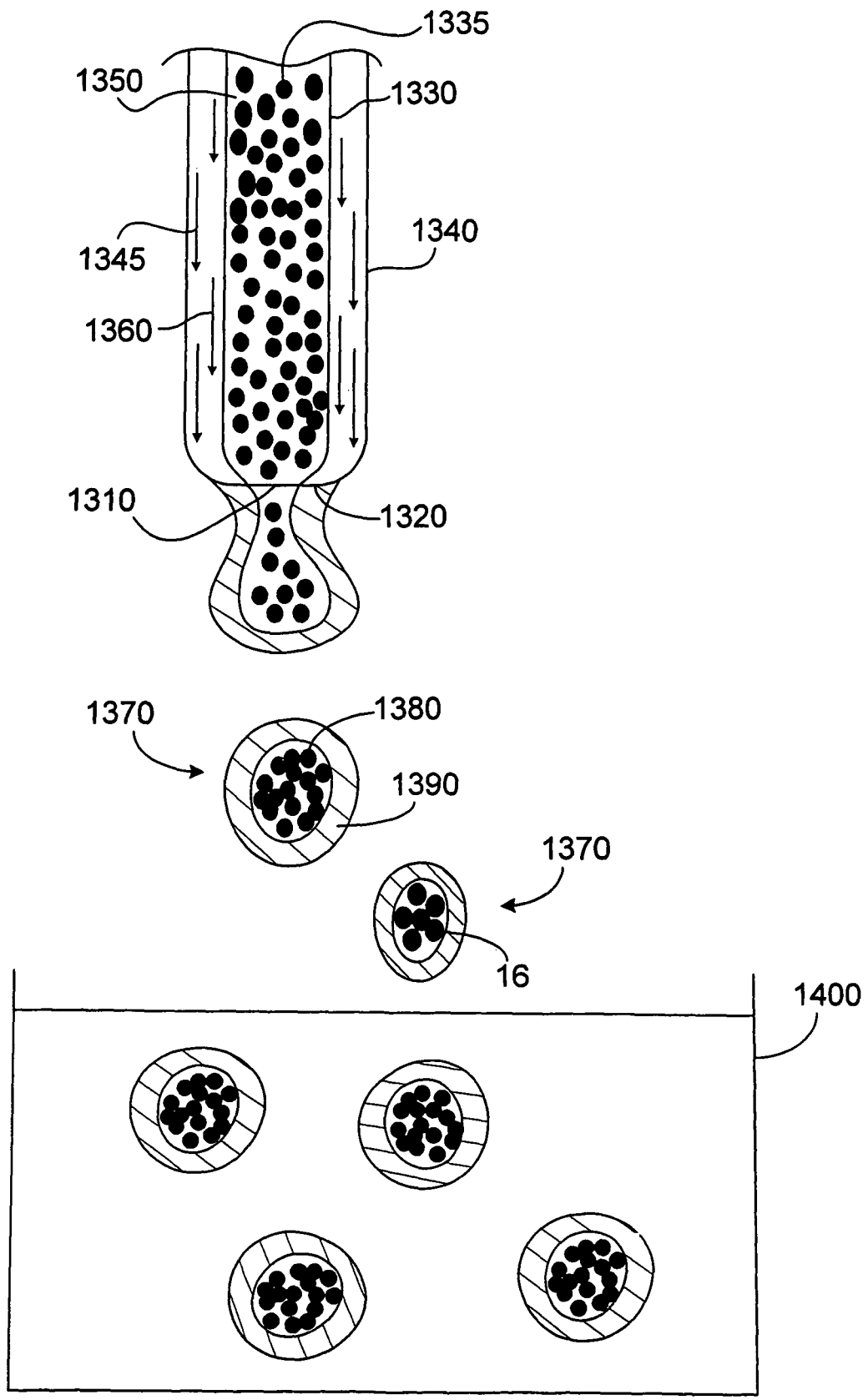
FIG. 6B is an illustration of the production of particles by the apparatus of FIG. 6A.

As shown in FIG. 6B, after being delivered to drop generator 1200, a stream 1350 of the gelling precursor mixture including ferromagnetic particles 16 passes through volume 1335 and exits inner nozzle 1330 via orifice 1310. Carbon dioxide is added to stream 1350 as stream 1350 passes through volume 1335. Thus, when stream 1350 exits inner nozzle 1330, stream 1350 includes bubbles of carbon dioxide gas. A stream 1360 of the polymer solution passes through volume 1345 and exits outer nozzle 1340 via orifice 1320. The streams interact as they exit the orifices. At the same time, nozzle 1300 is subjected to a periodic disturbance which results in the formation of drops 1370 having an interior region 1380 including gelling precursor, ferromagnetic particles 16, and carbon dioxide gas bubbles, and a polymer coating 1390. Drops 1370 fall into gelling vessel 1400, where the drops are stabilized by gel formation during which the alginate is converted from a solution form to a gel form. The gel-stabilized drops are then transferred from gelling vessel 1400 to reactor vessel 1500, where the polymer in the gel-stabilized drops is reacted, forming particles. Thereafter, the particles are filtered in filter 1700 to remove debris, and are sterilized and packaged as a composition including particles. In some embodiments, the particles are transferred, prior to filtration, to gel dissolution chamber 1600. In gel dissolution chamber 1600, the gelling precursor (which was converted to a gel) in the particles is dissolved. After the particle formation process has been completed, the particles can be filtered, sterilized, and packaged, as described above.

In some embodiments, the above-described process can be modified to produce particles having, for example, an internal pressure of at least about 1.1 atmospheres at a temperature of less than about 25° C. For example, the particles can be formed at a temperature of less than about 25° C. (e.g., at most about 20° C., at most about 15° C., at most about 10° C., at most about 5° C.). Alternatively or additionally, the particles can be formed in a pressurized environment (an environment having a pressure of greater than one atmosphere). For example, the particles can be formed in a chamber in which the pressure is at least about 1.1 atmospheres (e.g., at least about 1.2 atmospheres, at least about 1.5 atmospheres, at least about two atmospheres).

As another example, particles such as particle 300 (FIG. 4A) can be formed, for example, using the above-described drop generation process. In some embodiments, a mixture including water and ferromagnetic particles is flowed through volume 1335 of inner nozzle 1330, and a mixture including a solution (e.g., a polymer solution) is flowed through volume 1345 of outer nozzle 1340. After the particles have been formed, they can be frozen, such that the water forms ice pieces 306. In some embodiments, the particles may then be stored in a low-temperature environment, in order to limit premature melting by ice pieces 306.

As an additional example, particles such as particle 200 (FIG. 3) can be formed, for example, using the process described above with respect to FIGS. 5A and 5B. In some embodiments, two solutions (e.g., a polymer solution and a gelling precursor solution), either or both including ferromagnetic particles 206, can be flowed through concentric nozzle 1300 and mixed sufficiently to form drops that include a mixture of both solutions. Gas can be added into either or both solutions prior to mixing and/or after mixing. For example, a gelling precursor solution can be aerated with carbon dioxide gas prior to mixing, so that the gelling precursor solution includes carbon dioxide bubbles.

In certain embodiments, drop generator 1200 can be modified such that, instead of including concentric nozzle 1300, drop generator 1200 includes a single nozzle. A mixture (e.g., a polymer/gelling precursor mixture such as polyvinyl alcohol/alginate) including ferromagnetic particles 206 can then be flowed through the nozzle to form drops. In some embodiments, as the mixture is flowed through the nozzle, gas can be added into the mixture, so that the mixture includes bubbles of gas.

Particles such as particle 400 (FIG. 4B) can be formed, for example, by making particle 200 and soaking particle 200 in water, so that the water can enter some or all of pores 402.

In some embodiments, gas can be added into one or more of the mixtures or solutions that are used to make particles before the particle formation process has begun. As an example, a solution may be aerated with a gas, and then used in a particle formation process (as described above with reference to the formation of particle 200).

In certain embodiments, particles may be formed in a gaseous environment (e.g., in a chamber), such that the particles incorporate the gas during formation. In some embodiments, the gaseous environment can have a pressure of more than one atmosphere (e.g., at least about 1.1 atmospheres, at least about 1.2 atmospheres, at least about 1.5 atmospheres, at least about two atmospheres), and/or a temperature of less than about 25° C. (e.g., at most about 20° C., at most about 15° C., at most about 10° C., at most about 5° C.).

In some embodiments, one or more coatings can be applied to particles produced by any of the above-described processes, in order to help maintain the internal pressure within the particles. In certain embodiments, the particles can be formed in an environment having a low temperature and/or a high pressure, and can be coated while they still are in the environment having the low temperature and/or high pressure. In some embodiments, particles can be both formed and coated in a gaseous environment. Particles can be coated by, for example, spraying and/or dip-coating.

In certain embodiments, after particles have been formed, they may be stored in an environment having a low temperature (e.g., at most about 20° C.) and/or a high pressure (e.g., at least about 1.1 atmospheres). These storage conditions can help maintain the internal pressure of the particles and/or prevent the particles from bursting prematurely.

Methods of making particles are described, for example, in U.S. Patent Application Publication No. US 2004/0096662 A1, published on May 20, 2004, and in U.S. patent application Ser. No. 10/858,253, filed on Jun. 1, 2004, and entitled "Embolization", both of which are incorporated herein by reference.

While certain embodiments have been described, other embodiments are possible.

As an example, while particles that include (e.g., encapsulate) ferromagnetic particles have been described, in some embodiments, a particle can alternatively or additionally include a ferromagnetic material having a different shape or form. For example, a particle can include a ferromagnetic material in the form of a fiber, a flake, or a powder. In some embodiments, ferromagnetic particles, fibers, flakes, and/or powders can have a dimension (e.g., a diameter) of from about two microns to about 20 microns.

As another example, while particles that include carbon dioxide gas have been described, in some embodiments, a particle can alternatively or additionally include one or more other gases, such as nitrogen, oxygen, or water vapor. Typically, a gas that is included in a particle can be biocompatible.

As an additional example, while particles with a gelling precursor matrix and a polymer coating have been described, particles can have other types and combinations of materials. For example, in some embodiments, a particle can have a polymer matrix and a gelling precursor coating.

As a further example, while particles with coatings (e.g., polymer coatings) have been described, in some embodiments, a particle may not include a coating.

As another example, while particles including ferromagnetic material have been described, in some embodiments, a particle can include other types of materials that can be used to enhance an ablation procedure. For example, a particle may include (e.g., encapsulate) a sodium ion solution (e.g., a sodium chloride solution) and/or a calcium ion solution (e.g., a calcium chloride solution). When the particle bursts at a target site, the particle can release its contents to the target site, thereby enhancing ablation of the target site.

Figure 7:
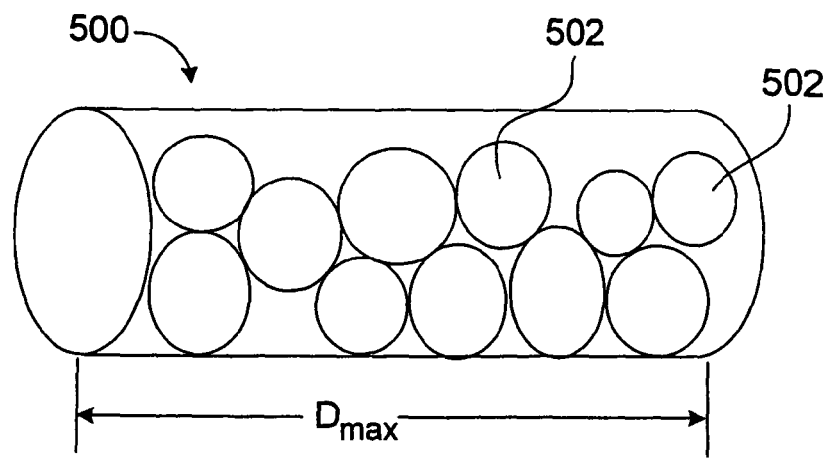
FIG. 7 is a side view of an embodiment of a capsule of particles.

As another example, in some embodiments, a capsule can be used to deliver one or more particles to a target site. For example, FIG. 7 shows a capsule 500 that contains particles 502. When capsule 500 is delivered to a target site (e.g., to the tissue of a subject), capsule 500 can separate, thereby releasing particles 502 into the target site.

Capsule 500 can be used, for example, to efficiently transport multiple particles 502 to a target site. In some embodiments, capsule 500 can be pressurized, and/or its contents can be maintained at a relatively low temperature, in order to limit the likelihood of premature bursting by particles 502. In some embodiments, capsule 500 can have an internal pressure of at least about 1.1 atmospheres (e.g., at least about 1.2 atmospheres, at least about 1.5 atmospheres, at least about two atmospheres), and/or a temperature of at most about 20° C. (e.g., at most about 15° C., at most about 10° C., at most about 5° C.). As shown in FIG. 7, capsule 500 has a maximum dimension $D_{max}$. In some embodiments, maximum dimension $D_{max}$ can be from about 3,000 microns to about 5,000 microns. While capsule 500 is generally cylindrical in shape, in certain embodiments, a capsule can have a different shape. For example, a capsule can be spherical or spheroidal.

As a further example, in some embodiments, particles can be used in an RF ablation procedure that employs a coaxial electrode (e.g., a 3.5 centimeter coaxial LeVeen electrode, available from RadioTherapeutics, Mountain View, Calif.).

Figure 8A:
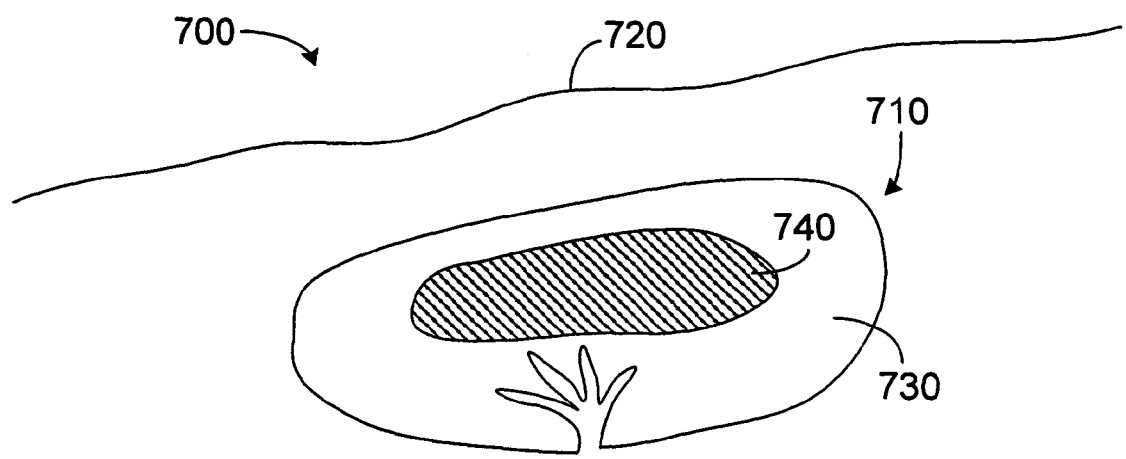
FIG. 8A is a cross-sectional view of a liver of a subject.
Figure 8B:
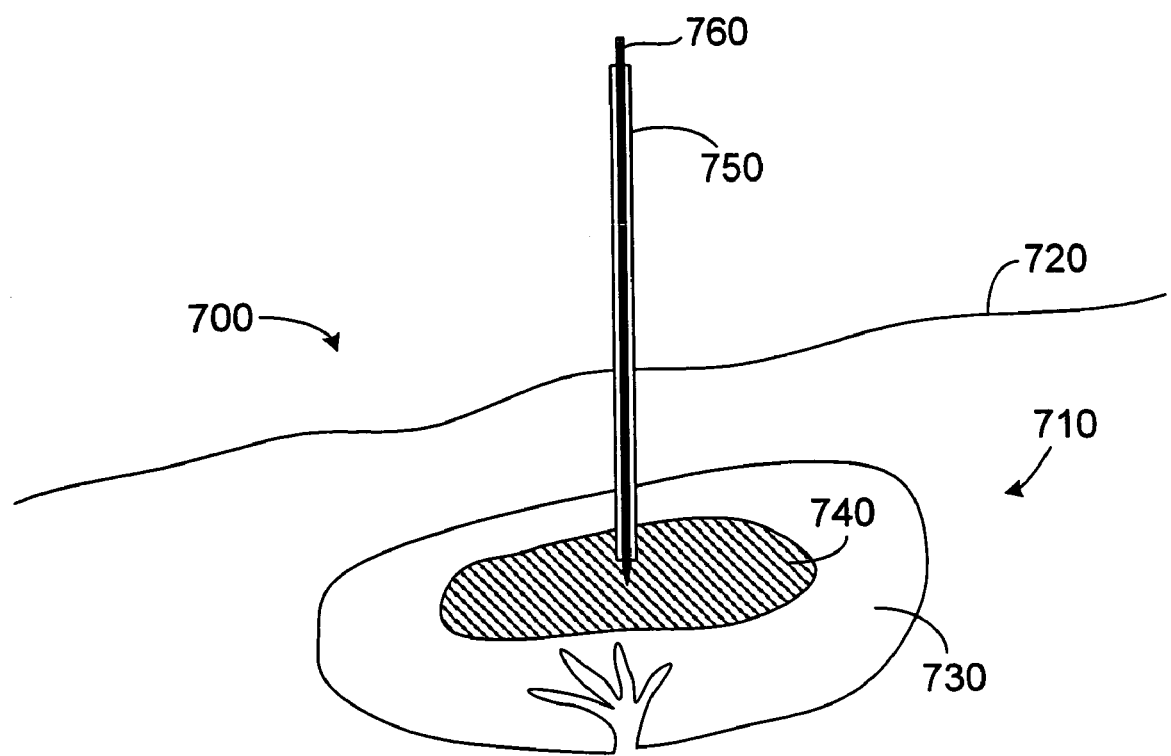
FIG. 8B illustrates delivery of a cannula into the liver of FIG. 8A.
Figure 8C:
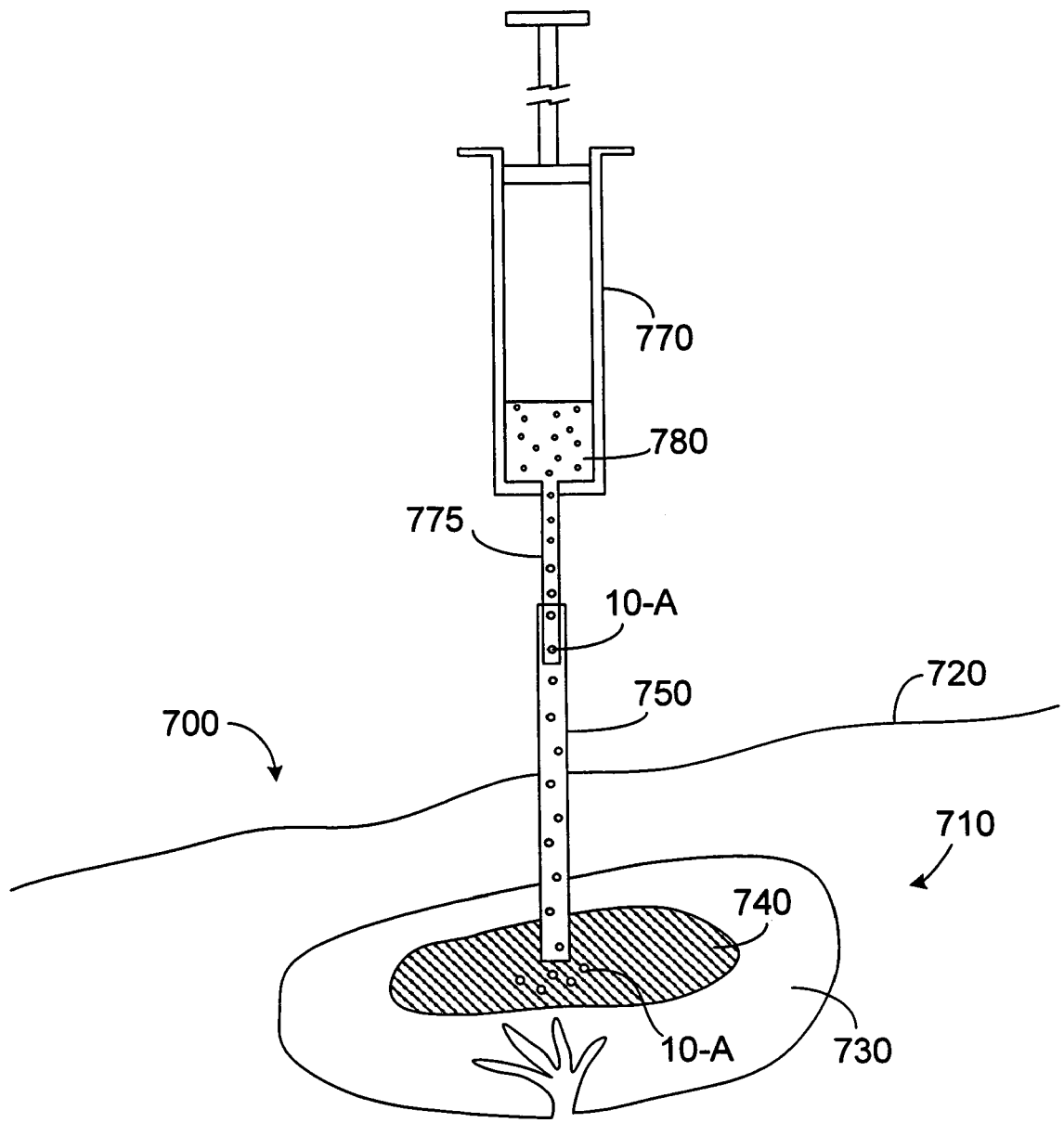
FIG. 8C illustrates administration of particles into the liver of FIG. 8A.

For example, FIG. 8A shows a portion 700 of a subject including a liver 710 and skin 720. Liver 710 includes healthy tissue 730 and unhealthy tissue 740. FIG. 8B illustrates the delivery of a cannula 750 into unhealthy tissue 740, using a trocar 760. After cannula 750 has been delivered into unhealthy tissue 740, trocar 760 is removed from cannula 750 and, as shown in FIG. 8C, needle 775 is inserted into cannula 750. Needle 775 is in fluid communication with a syringe 770, which contains a composition including particles 10-A suspended in a carrier fluid 780. Particles 10-A and carrier fluid 780 are injected from syringe 770, through needle 775 and cannula 750, and into unhealthy tissue 740. After particles 10-A and carrier fluid 780 have been delivered, needle 775 and syringe 770 are removed from cannula 750.

Figure 8D:
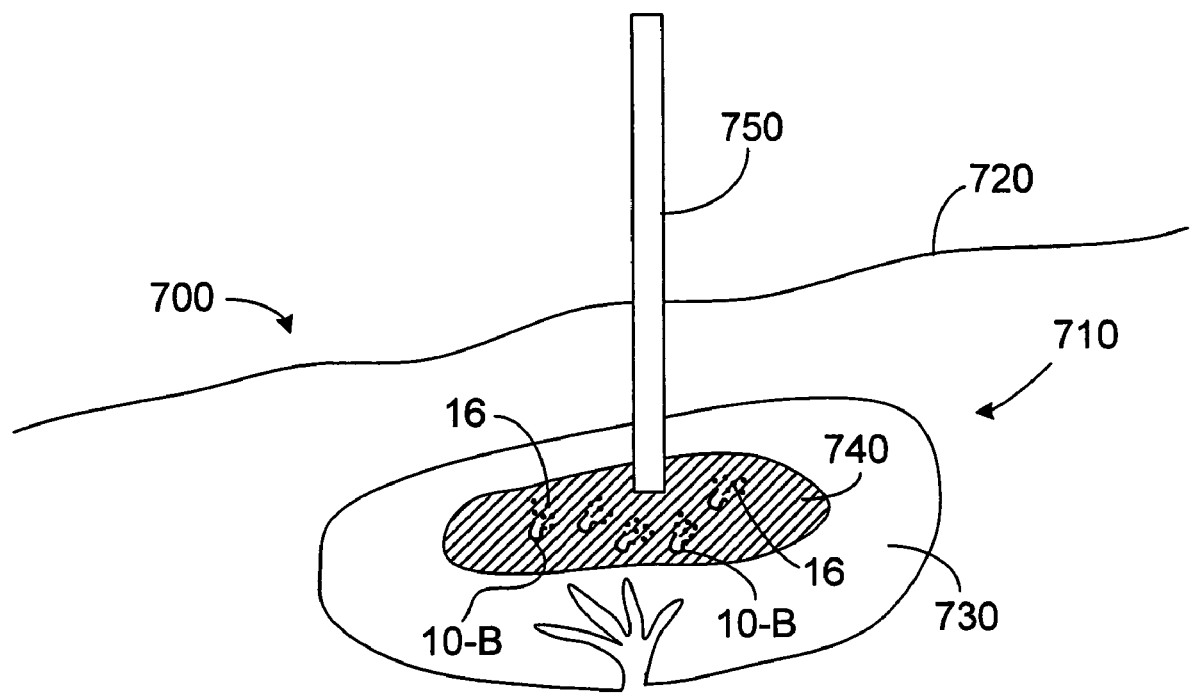
FIG. 8D is a cross-sectional view of the liver of FIG. 8A, after the particles have been administered into the liver.

While particles 10-A are generally intact when first delivered into unhealthy tissue 740 (as shown in FIG. 8C), as particles 10-A are heated to body temperature (about 37° C.), particles 10-A burst, thereby forming burst particles 10-B, and releasing ferromagnetic particles 16 into unhealthy tissue 740 (as shown in FIG. 8D).

Figure 8E:
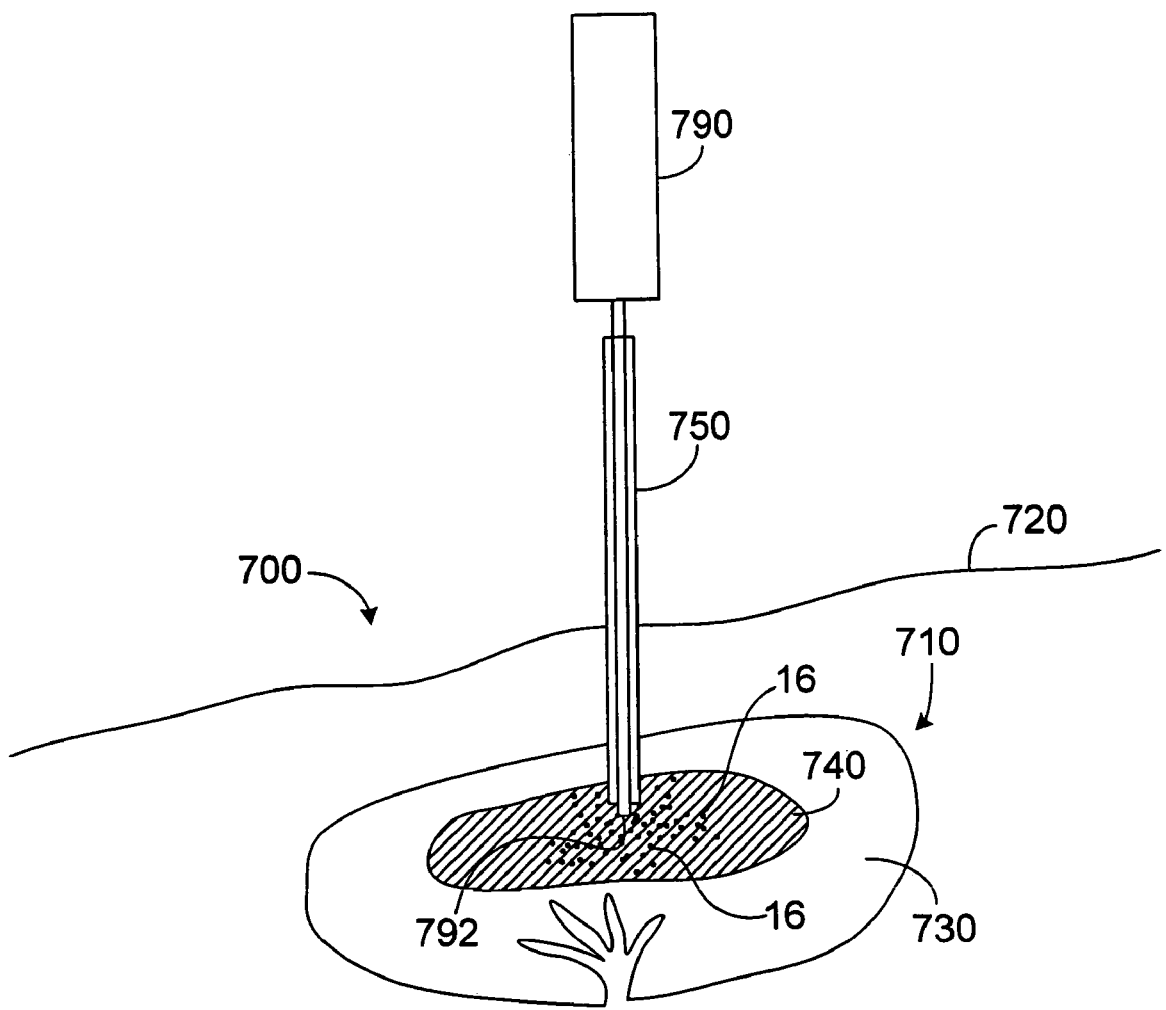
FIG. 8E illustrates delivery of an RF electrode into the liver of FIG. 8A.
Figure 8F:
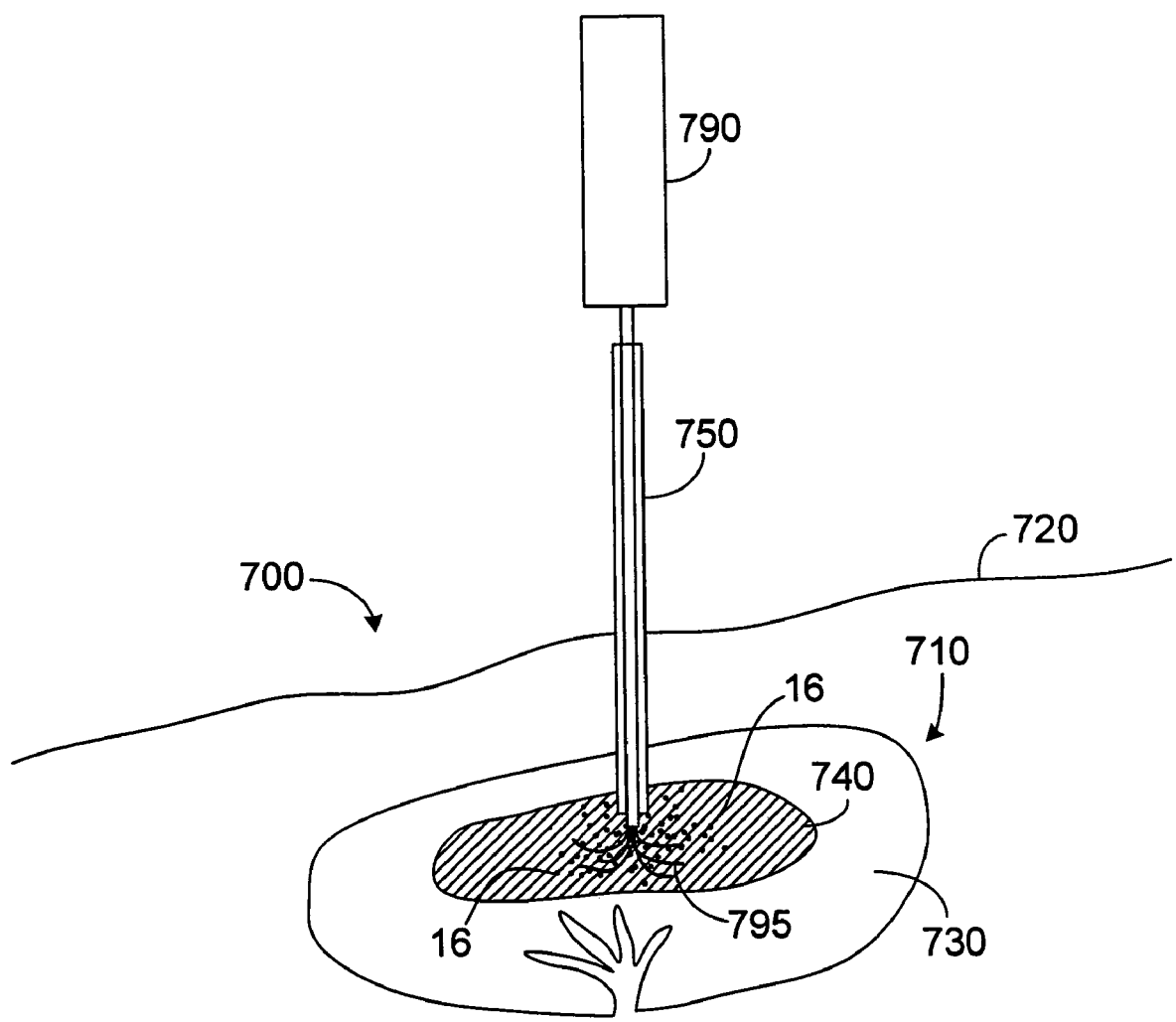
FIG. 8F illustrates an RF electrode with tines deployed within the cancerous tissue region of the liver of FIG. 8A.
Figure 9:
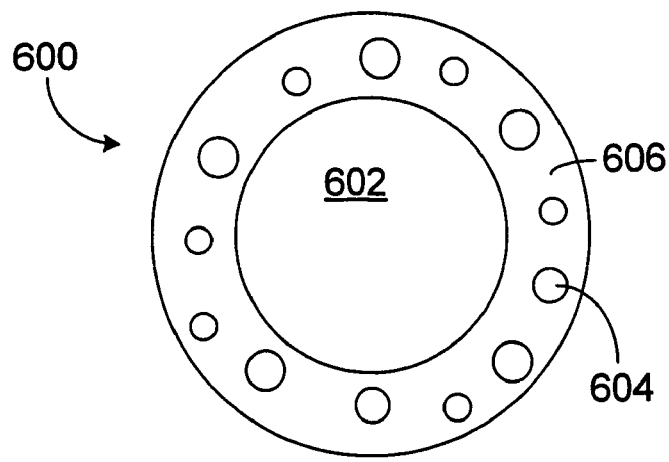
FIG. 9 is a cross-sectional view of an embodiment of a particle.

As FIG. 8E shows, an RF electrode 790 is then inserted into cannula 750, such that its distal end 792 enters unhealthy tissue 740. As shown in FIG. 8F, tines 795 are thereafter deployed within unhealthy tissue 740. RF electrode 790 can subsequently be activated so that RF energy is emitted from tines 795.

As another example, in certain embodiments, an RF electrode can be used to increase the temperature of one or more particles (e.g., particles that include ferromagnetic material) at a target site (e.g., within cancerous tissue of a subject). In some embodiments, this increase in the temperature of the particles can cause the particles to burst.

As a further example, in some embodiments in which particles release ferromagnetic material (e.g., ferromagnetic particles) at a target site (e.g., tissue of a subject), the ferromagnetic material can be used in an agitation ablation process. In such a process, a magnetic field can be used to agitate the ferromagnetic material, such that the ferromagnetic material heats and/or physically deforms the surrounding target site, thereby ablating the surrounding target site.

As another example, in certain embodiments, a laser can be used to ablate a target site (e.g., in which particles have released ferromagnetic material).

As an additional example, in some embodiments, a particle can be contacted with an agent (e.g., an alcohol, hydrochloric acid, sodium hydroxide, sodium citrate, sodium hexa-metaphosphate) that can dissolve or erode at least a portion of the particle. The agent can be used, for example, to accelerate the bursting of the particle. The agent can be applied to the particle prior to, during, and/or after delivery of the particle to a target site. For example, in some embodiments in which a particle includes a sodium alginate coating, at least a portion of the sodium alginate coating can be dissolved by contacting the coating with sodium hexa-metaphosphate.

As a further example, in some embodiments, a particle (either porous or non-porous) can include at least one cavity (a hollow central region in the particle). In certain embodiments in which a particle includes a cavity, the particle can further include pores in the material surrounding the cavity. The particles can include one or more gases in the cavity and/or pores. For example, FIG. 8 shows a particle 600 with a cavity 602 surrounded by a matrix material 606 (e.g., a polymer) that includes pores 604.

As another example, in some embodiments, a particle can include a shape memory material, which is capable of being configured to remember (e.g., to change to) a predetermined configuration or shape. In certain embodiments, particles that include a shape memory material can be selectively transitioned from a first state to a second state. For example, a heating device provided in the interior of a delivery catheter can be used to cause a particle including a shape memory material to transition from a first state to a second state. Shape memory materials and particles that include shape memory materials are described in, for example, U.S. Patent Application Publication No. US 2004/0091543 A1, published on May 13, 2004, and U.S. patent application Ser. No. 10/791,103, filed Mar. 2, 2004, and entitled "Embolic Compositions", both of which are incorporated herein by reference.

As an additional example, in some embodiments, a particle can include a surface preferential material. Surface preferential materials are described, for example, in U.S. patent application Ser. No. 10/791,552, filed on Mar. 2, 2004, and entitled "Embolization", which is incorporated herein by reference.

As a further example, in certain embodiments, particles can be linked together to form particle chains. For example, the particles can be connected to each other by links that are formed of one or more of the same material(s) as the particles, or of one or more different material(s) from the particles. Particle chains and methods of making particle chains are described, for example, in U.S. patent application Ser. No. 10/830,195, filed on Apr. 22, 2004, and entitled "Embolization", which is incorporated herein by reference.

As an additional example, in some embodiments one or more particles is/are substantially nonspherical. In some embodiments, the particles can be mechanically shaped during or after the particle formation process to be nonspherical (e.g., ellipsoidal). In certain embodiments, particles can be shaped (e.g., molded, compressed, punched, and/or agglomerated with other particles) at different points in the particle manufacturing process. As an example, in certain embodiments in which the particles are formed using a gelling agent, the particles can be physically deformed into a specific shape and/or size after the particles have been contacted with the gelling agent, but before the polymer(s) in the particles have been cross-linked. After shaping, the polymer(s) (e.g., polyvinyl alcohol) in the particles can be cross-linked, optionally followed by substantial removal of gelling precursor (e.g., alginate). While substantially spherical particles have been described, in some embodiments, nonspherical particles can be manufactured and formed by controlling, for example, drop formation conditions. In some embodiments, nonspherical particles can be formed by post-processing the particles (e.g., by cutting or dicing into other shapes). Particle shaping is described, for example, in Baldwin et al., U.S. Published Patent Application No. US 2003/0203985 A1, which is incorporated herein by reference.

Figure 10A:
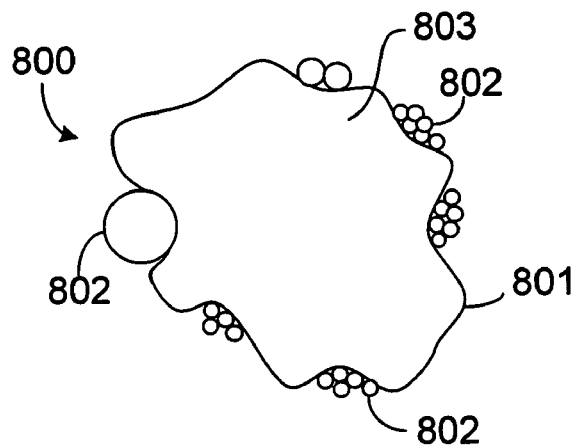
FIG. 10A is a cross-sectional view of an embodiment of a particle.
Figure 10B:
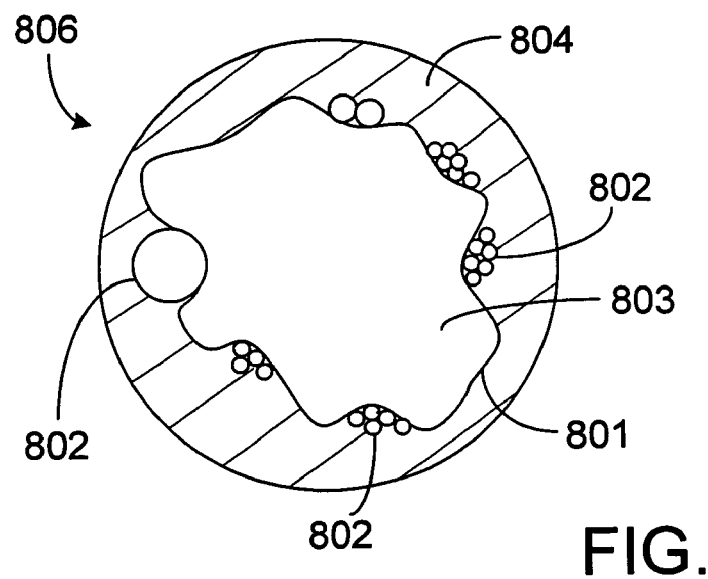
FIG. 10B is a cross-sectional view of an embodiment of a particle.

As a further example, in certain embodiments, nonspherical (e.g., irregular) particles can be formed and exposed to a gaseous atmosphere, such that the particles may trap gas bubbles on their surface. In some embodiments, the particles may thereafter be coated. For example, FIG. 10A shows an irregular particle 800 including a body region 803 having a surface 801. Gas bubbles 802 are trapped on surface 801 of body region 803. FIG. 10B shows a particle 806 including body region 803, gas bubbles 802, and a coating 804.

As another example, in some embodiments a solution can be added to the nozzle of a drop generator to enhance the porosity of particles produced by the drop generator. Examples of porosity-enhancing solutions include starch, sodium chloride at a relatively high concentration (e.g., more than about 0.9 percent, from about one percent to about five percent, from about one percent to about two percent), and calcium chloride (e.g., at a concentration of at least about 50 mM). For example, calcium chloride can be added to a sodium alginate gelling precursor solution to increase the porosity of the particles produced from the solution.

As an additional example, in some embodiments, particles having different shapes, sizes, physical properties, and/or chemical properties, can be used together in a procedure (e.g., an ablation procedure). The different particles can be delivered into the body of a subject in a predetermined sequence or simultaneously. In certain embodiments, mixtures of different particles can be delivered using a multi-lumen catheter and/or syringe. Particles with different shapes, sizes, physical properties, and/or chemical properties are described, for example, in U.S. Patent Application Publication No. US 2004/0091543 A1, published on May 13, 2004, and in U.S. patent application Ser. No. 10/791,103, filed Mar. 2, 2004, and entitled "Embolic Compositions", both of which are incorporated herein by reference.

Other embodiments are in the claims.

What is claimed is:

1. A particle having an internal pressure of at least about 1.1 atmospheres and at most about 5.0 atmospheres at a temperature of less than about 25° C., wherein the particle has a diameter of at most about 3,000 microns and the particle bursts at a temperature of at most about 200° C., and
   wherein the particle comprises a gas generator, and when the gas generator is heated to a temperature of at least about 25° C., the internal pressure of the particle increases to at least about 1.2 atmospheres.

2. The particle of claim 1, wherein the gas generator is disposed in an interior region of the particle.

3. A particle having an internal pressure of at least about 1.1 atmospheres and at most about 5.0 atmospheres at a temperature of less than about 25° C., wherein the particle has a diameter of at most about 3,000 microns and the particle bursts at a temperature of at most about 200° C., and
   wherein the particle comprises a gas generator, and when the gas generator is heated to a temperature of at least about 35° C., the internal pressure of the particle increases to at least about 1.5 atmospheres.

4. A particle having an internal pressure of at least about 1.1 atmospheres and at most about 5.0 atmospheres at a temperature of less than about 25° C., wherein the particle has a diameter of at most about 3,000 microns and the particle bursts at a temperature of at most about 200° C., and
   wherein the particle comprises a gas generator, and when the gas generator is heated to a temperature of at least about 90° C., the internal pressure of the particle increases to at least about 1.5 atmospheres.

5. A particle having an internal pressure of at least about 1.1 atmospheres and at most about 5.0 atmospheres at a temperature of less than about 25° C., wherein the particle has a diameter of at most about 3,000 microns and the particle bursts at a temperature of at most about 200° C., and
   wherein the particle comprises a gas generator, and when the gas generator is heated to a temperature of at least about 100° C., the internal pressure of the particle increases to at least about 1.5 atmospheres.

6. The particle of claim 5, wherein the gas generator comprises water or saline.

* * * * *